(12) United States Patent
Sprycha et al.

(10) Patent No.: US 7,886,590 B2
(45) Date of Patent: Feb. 15, 2011

(54) APPARATUS AND METHOD FOR QUANTITATIVELY MEASURING LIQUID FILM DRYING RATES ON SUBSTRATES

(75) Inventors: Ryszard Sprycha, Wallington, NJ (US);
Doreen E. Smith, Belleville, NJ (US);
David Biro, Rockaway, NJ (US);
Juanita Parris, Montvale, NJ (US);
Mikhail Laksin, Boonton, NJ (US);
Gregory Pace, Wood-Ridge, NJ (US)

(73) Assignee: Sun Chemical Corporation, Parsippany, NJ (US)

( * ) Notice: Subject to any disclaimer, the term of this patent is extended or adjusted under 35 U.S.C. 154(b) by 1103 days.

(21) Appl. No.: 10/522,972

(22) PCT Filed: Aug. 8, 2003

(86) PCT No.: PCT/US03/25137
§ 371 (c)(1),
(2), (4) Date: Mar. 21, 2008

(87) PCT Pub. No.: WO2004/015379
PCT Pub. Date: Feb. 19, 2004

(65) Prior Publication Data
US 2008/0209996 A1     Sep. 4, 2008

Related U.S. Application Data

(60) Provisional application No. 60/401,957, filed on Aug. 8, 2002.

(51) Int. Cl.
*G01N 17/00* (2006.01)
*G01B 21/08* (2006.01)
(52) U.S. Cl. .................................. 73/150 R
(58) Field of Classification Search ............... 73/150 R
See application file for complete search history.

(56) References Cited

U.S. PATENT DOCUMENTS 3,881,349 A    5/1975    Stone (Continued)

FOREIGN PATENT DOCUMENTS

EP         0405587 A       1/1991

(Continued)

OTHER PUBLICATIONS

Carreira Leonard et al.; "Correlation between drying time and ink jet print quality parameters," Proceedings of the 1995 IS&T's 11th International Congress on Advances in Non-Impact Printing Technologies; Hilton Head, SC, USA, Oct. 29-Nov. 3, 1995, p. 334-337.

(Continued)

*Primary Examiner*—Hezron Williams
*Assistant Examiner*—Nathaniel Kolb
(74) *Attorney, Agent, or Firm*—Kramer Levin Naftalis & Frankel LLP

(57) ABSTRACT

An apparatus and method for measuring the drying rate of a liquid or liquid film in air or other gaseous media by either: a) measuring changes in the print density of the liquid; b) measuring changes in the dynamic surface tension of the liquid; c) measuring the differential pressure between an inert gas required to displace a sample of the liquid drawn into a capillary tube from a reservoir of the liquid and the pressure required for a bubble of the gas to form in the reservoir; and d) measuring the electrical conductance or resistance of the liquid.

11 Claims, 20 Drawing Sheets

U.S. PATENT DOCUMENTS 5,140,902 A    8/1992   Schneider
5,503,682 A    4/1996   Mueller-Kirschbaum et al.
5,572,115 A    11/1996  Strong et al.
6,475,602 B1 * 11/2002  Kapusniak et al. ....... 428/32.34

OTHER PUBLICATIONS

Sarada T: "Ink Jet Printing on Plain Paper," 1984 International Printing & Graphic Arts/Testing Conference, Proceedings of the Technical Association of the Pulp and Paper Industry, Niagara Falls, NY, USA, 1984, pp. 57-62.

ASTM Standard D1640-95, Apr. 1995, paragraphs 6.1.-7.9.

Durieux Eric et al., "An Analysis of Ink Jet Ink and Untreated Vinyl Interactions," Int. Conf. Digit. Print. Technol.; International Conference on Digital Printing Technologies 2000, pp. 501-506.

Fainerman V B et al., "The Measurement of Dynamic Surface Tension by the Maximum Bubble Pressure Method," Colloid & Polymer Science, Darmstadt, DE, vol. 272, No. 6, 1994, pp. 731-739.

Dissado L A et al: "Power-Law Decay of Conductance During the Drying of Latex Paints," Journal of Physics D. Applied Physics, IOP Publishing, Bristol, GB, vol. 22, No. 5, May 14, 1989, pp. 713-716.

International Search Report, Application No. PCT/US03/25137, Dated Jan. 27, 2004.

European Search Report, Application No. 03785193, Dated Aug. 30, 2005.

* cited by examiner

MAXIMUM BUBBLE PRESSURE
(MBP) METHOD

SET-UP FOR DETERMINATION OF INK DRYING — SCHEMATIC DIAGRAM

TAIL vs. AVER INITIAL & AFTER DENSITY
FLEXOMAX ON SBS

TAIL vs. AVER INITIAL & AFTER DENSITY
FLEXOMAX ON FILM

DRYING RATE - 33 vs. 039 FLEXOMAX BLUE INKS

FLEXOMAX 33 vs. 039 - (MAYER BAR #13)

W-b FLEXO INKS - FAST (88A) vs. SLOW (88C) MAYER BAR #13

W-b FLEXO INK - 88A - HANDPROOFER 120lpi

APPARATUS AND METHOD FOR QUANTITATIVELY MEASURING LIQUID FILM DRYING RATES ON SUBSTRATES

FIELD OF THE INVENTION

This invention relates to the determination and indirect measurement of liquids and liquid films. The invention also relates to apparatus and methods for determining the drying rate of liquid films applied on a substrate.

BACKGROUND OF THE INVENTION

The need to determine the drying rate of a liquid film applied on a substrate frequently arises in a wide variety of contexts and industrial applications such as printing inks, paints, coatings, lacquers, electronics, etc. For instance, printing ink in its supply form is liquid (low viscosity liquids such as gravure or ink-jet inks or high viscosity liquids such as letterpress or lithographic inks) but changes to a solid form after its application.

This change from liquid to solid state (drying) may occur in many ways:

Evaporation drying—where the rate of drying depends on the evaporation rate of the solvents used;

Oxidation drying—where the liquid dries by oxidation as a result of chemical reaction between the liquid and oxygen from the atmosphere;

Absorption drying—where the liquid and/or solvents can penetrate into the porous structure of the substrate;

Chemical drying—different than oxidation mechanism e.g. thermosetting liquid such as inks or paints, here chemical cross linking takes place at the elevated temperatures; and Radiation curing—where polymerization of monomers and oligomers used in the liquid takes place when the liquid ink film is irradiated with ultraviolet (UV) light or an electron beam (EB).

Additional details on the different mechanisms for liquid drying can be found for printing inks in "The Printing Ink Manual" by R. Leach and R. Pierce, $5^{th}$ Edition, copyright 1993.

Typically, liquids such as printing inks have been reported to dry on the basis of a simple scale having gradations ranging from "quick or fast drying" to "medium drying" and "slow drying". The determination of which of the three drying rate categories a particular liquid should be classified in has usually been done on the basis of visual and/or tactile inspection. In this regard a sample of the liquid is applied wet to a substrate material, typically glass or metal, and the degree of dryness is visually or physically observed over certain predetermined time periods. The liquid is observed over a range of time between several seconds to hours in duration, at which times the visual appearance of the sample is noted and/or the surface of the sample is contacted or touched in order to determine the tackiness of the sample. Thus, a sample is determined to be either dry or still drying and is correspondingly assigned either a "quick or fast drying", "medium drying", or "slow drying" designation. This method is extremely subjective and non-quantitative.

The appropriate drying rate of an ink, if not known, can cause severe problems for printers. For instance, during printing with gravure or flexographic inks the ink may dry in the gravure cylinder or anilox roller cells. The dry ink can clog the cells of, for example, a printing cylinder and make printing impossible. Therefore, the drying rate of the ink is extremely important and has to be appropriately balanced to achieve the expected result, e.g. high printing speed and high quality prints. An ink drying too fast may affect ink transfer in flexographic and gravure printing since the ink will dry either too fast or too slow on the plate, rollers or cells. Further printing problems include clogged print head nozzles and poor print quality in the final product, e.g. ink jet printing.

Another method used is a Geiger Press Test wherein the resolubility of a "dry" liquid is determined by applying ink onto the drying liquid film in a simulation of stopping and re-starting a press and having the same printability as previous to the stoppage. If the "dried" film resolubilizes, the number of proofs necessary to get back to original state is noted and a drying classification and resolubility classification is determined for that liquid film. Again, this test is subjective and non-quantitative.

Moreover, it is extremely difficult or impossible to make any evaluation when the liquid dries very rapid. There are some instruments available in the market that allow for a less-subjective evaluation of liquid drying such as the PIRA ink drying time tester, the IGT drying time recorder, and the Thin Film Analyzer (TFA). These instruments are based on different principles and can be used only for high viscosity and relatively thick liquid films (e.g. paints, coatings). They cannot be used to evaluate the drying rate of low viscosity, fast drying and relatively thin liquid films.

At the present, there is no instrument capable of quantitatively characterizing the drying rate of liquids and liquid films. There is a need in the art for a technique of measuring the drying rate of liquids and/or liquid films applied or to be applied to a substrate on a more precise, quantitative, basis. Because there is no simple way to directly measure the parameter "drying rate", it is, alternatively, necessary to measure some other physical property related to the liquidity or fluidity, that conversely relates to the degree of dryness of the liquid being measured.

The drying rate of the liquid may also affect some experimental techniques used to characterize the properties of liquids such as, e.g., dynamic surface tension (DST). The instruments that are used to measure the DST use the maximum bubble pressure (MBP), such as the BP2 tensiometer by Kruss, USA, or to measure the differential maximum bubble pressure (DMBP), such as the PC9000 by Sensadyne, USA, are techniques which utilize a single or multiple capillaries immersed in the liquid, respectively. Gas is forced through the capillaries and its flow rate and the back pressure is measured to calculate the DST of the liquid. However, liquids that dry fast and have inadequate resolubility dry inside the capillaries and substantially affect the DST (i.e. pressure) measurements.

While others have determined the surface tension of a liquid using DST measurements, no one has associated the DST (pressure) measurements with the drying rate of liquids or proposed this principle as a method to quantify the drying rate of liquids. The DST of liquids can be measured with relative ease. For example, U.S. Pat. No. 3,881,344 entitled "Monitor for Continuously Measuring Surface Tension of Liquids" discloses an apparatus for measuring the DST of a liquid in a flowing stream, whereby a capillary tube is dipped in the liquid and a gas bubble is formed on the end of the tube by forcing air down the tube. The pressure required to form the bubble at the capillary tip below the liquid surface is related to the surface tension of the liquid via the following expression:

$$\gamma = (d\Delta P)/4$$

where:
- γ is the dynamic surface tension in dynes/cm or mN/m;
- d is the effective diameter of the capillary tube in cm; and
- ΔP is the excess of the inert gas pressure required to generate bubbles at the capillary tip immersed in the liquid at a given rate, in dynes/cm$^2$.

However, the association between this pressure (or the DST of the liquid) and the drying rate of a liquid has not been explored and developed.

Moreover, there exists a need to be able to quantitatively measure the drying rate of a liquid by virtue of monitoring the changes in electrical conductance and resistance associated with the liquid as it dries. Such a test is needed which would be industrially suitable for applications involving printing inks, paints, coatings, varnishes, lacquers, adhesives and the like. This would include gravure and flexographic inks, such as water based and solvent based liquid inks and for paper packaging and solvent based and water based inks for film. More specifically, evaluation of the degree of cure (i.e. drying) of an ultraviolet (UV) or electron beam (EB) cured ink and/or coating is a very important issue for all printers that use energy curable (EC) inks and, for example, coatings. Such evaluation can be done in the lab using very sophisticated instrumentation, such as chromatography and spectroscopy. However, there is currently no method and instrument presently available that would allow for quick and easy degree of cure measurement. The industrial test currently used (a solvent rub test) is off-line and is very subjective and irreproducible. There is a high demand in the market for an instrument and a method capable of quickly quantifying and determining the degree of cure for EC ink and/or coating formulations. In addition, no one has developed a way to quickly measure the drying rate of conventional or EC inks and coatings.

SUMMARY OF THE INVENTION

Accordingly, the invention is an apparatus and method for determining the drying rate of a liquid applied on a substrate, which provides quantitative measurement correlated with the drying rate of the liquid applied on the substrate.

According to another embodiment of the invention, there is provided an apparatus and method for measuring DST (pressure) and correlating this to the drying rate of a liquid and/or liquid film.

According to another embodiment of the invention, there is provided an apparatus and method for quantitatively measuring the drying rate of liquids based on the print density of a liquid at certain intervals after it has been rolled out on a substrate.

According to another embodiment of the invention, there is provided an apparatus and method for directly measuring the electrical conductance or inversely the electrical resistance of a liquid as representative of the drying rate of the liquid or liquid film.

According to another embodiment of the invention, there is provided an on-line apparatus and method for directly measuring the electrical conductance or inversely the electrical resistance of an energy curable liquid and capable of correlating it to the drying rate of the energy curable liquid.

DETAILED DESCRIPTION OF THE INVENTION

The invention of quantitatively measuring the drying rate of a liquid applied to a substrate is described herein along with the corresponding apparatus for measuring the drying rate of a liquid applied to a substrate.

Print Density Method

A method is disclosed wherein the drying rate of a liquid applied to a substrate is quantitatively measured by the print density of the liquid at certain intervals of the liquid being applied onto the substrate.

Generally, according to the method, a controlled volume of the liquid to be tested is applied to an application means such as a handproofer and is rolled-out on a substrate material, to form an initial (I) proof. The ink on the application means is allowed to dry over a pre-determined period of time, then re-applied to the application means and rolled-out on a fresh substrate, to form the after (A) proof. A densitometer is used to read the end of each "tail" of the rollouts providing a print density or density number. The "tail" is the visible change in density of the liquid on the substrate as it is being rolled out on the substrate. The tail is then read by a densitometer in order to determine the density of each separate tail.

The density reading data obtained from the rollouts is used to determine the drying time of the liquid, which is calculated based on the number of tails and the density of each tail. The density reading data is then used to plot a curve, for the I proof and the A proof and subsequent I and A curves are then graphed. The area between the curves is then calculated and the coefficients of an empirical model are determined.

Figure 1:
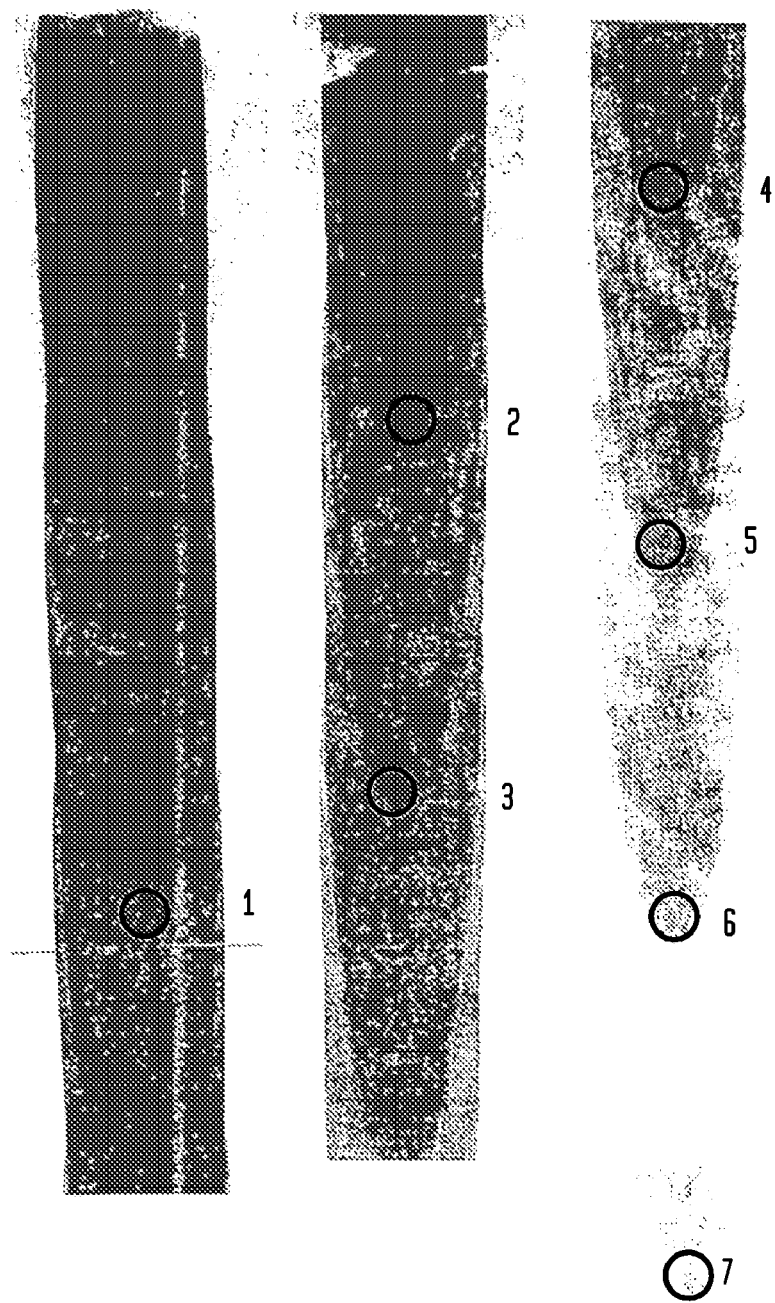
FIG. 1 is an overall view of the roll out and drying rate of a liquid as correlated and measured by the density of the liquid after its application on a substrate.

The method includes loading a liquid in a set volume, which can be any volume, as long as repeated throughout the method, onto an application means. For tests of drying rate of an ink on a substrate, the ink should be tested at its press viscosity. The liquid is discharged through a disposable pipet tip and one pipet should be used per rollout and not reused due to potential clogging problems. As seen in FIG. 1, the liquid film is applied to a substrate via any conventional application apparatus including a flexo press or handproofer, such as an Early Enterprises Handproofer. An initial (I) rollout from the application apparatus is made onto the substrate utilizing a constant angle, pressure and speed of application. The substrate may be made of paper or film. Suitable substrates include paper, plastics, glass, film or the like. For tests on a film substrate, a film such as AET Films T 523-3 is preferred. As necessary according to the liquid applied, film samples are oven dried at a temperature of around 80° C. for the time necessary to cure. After sufficient time, preferably around 5 minutes, for the liquid to dry on the application apparatus, the liquid is once again applied to the application apparatus in the same volume and rolled out on the same type of substrate via a new pipet tip, again using constant angle, pressure and speed. This is referred to as the after (A) rollout.

The overall method is repeated as many times as necessary in order to arrive at an average graph or model fit through data analysis.

The tail of each rollout is located and marked with a circle for scanning into a densitometer. Multiple repetitions of the I and A rollouts are preferably performed so that the average values and/or model fit can be determined.

Once the average and/or model fit density of each tail is calculated, the average and/or model fit density is plotted on a graph versus the tail number for both the I rollout and the A rollout. The slope of curve of the I and A rollouts are referred to as the I drying proof curve and the A drying and resolubility proof curve. The I curve represents drying, transfer and absorption. The A curve represents drying, transfer, absorption and resolubility. The area between the I and A curves represents both the resolubility and the drying rate of the liquid.

Generally, it was found that faster drying liquids had less tails and a greater slope of the curves. Correspondingly, slower drying liquids had more tails and a smaller slope of the curves.

The method allows liquids to be distinguished on the basis of their drying rate and resolubility. The method may also be used to test the multiple (typically four or more) colors of a process ink set to determine whether all colors print process equally, dry at the same rate and therefore set together so as to determine if different diluting solvents are required for the inks of the same process set to have good printability. Thus, the method can also be used to differentiate between liquid inks for drying and resolubility to determine if cutting solvent mixture needs to be changed for a particular pigment. The method can also be applied to traps and used to predict the tracking and trapping of the liquid in question. Tracking is noted on a substrate due to poor drying while smearing on the substrate might be due to poor resolubility. One of the reasons for poor trapping may be poor drying and poor resolubility wherein one ink dries either too fast or too slow before the trapped ink is applied and can result in increased costs to the press when it occurs. The method may also be used to distinguish between process and non-process printers in that the process printers must be slow drying in order to reproduce the print required in sufficient clarity. For example, differences have been observed between magenta and cyan color inks within the same base system.

DST Method

A further apparatus and method for measuring the drying rate of a liquid is disclosed using the discovered relation between the pressure (or the apparent DST of the liquid) necessary to generate a bubble at the capillary tip immersed in a liquid, as the liquid dries and therefore clogs the capillary reducing the radius of the capillary, and the related drying rate of said liquid.

Surface tension is commonly measured using static, equilibrium techniques such as the duNouy tensiometer. DST measurement thus frequently uses the maximum bubble pressure method (single capillary) or the DMBP method (two capillaries of different orifices). Gas passes through an orifice tube into a liquid, forming a succession of bubbles. The inflation pressure inside each bubble is at a maximum when the bubble achieves minimum radius of curvature equal to the capillary as established in Equation (1) above. The maximum bubble pressure occurs as the bubble assumes hemispherical shape at the orifice. The maximum bubble pressure is thus directly related to, and provides a true measure of, the surface tension of the liquid. (W. J. Moore, Physical Chemistry, 3rd Ed., p. 729-31, Prentice Hall, N.J., 1962.). Using these instruments, maximum bubble pressure is observed as a value averaged over a number of bubbles generated at a fixed rate. When more than one rate is to be studied, the rate of bubbling must be changed manually or automatically, and another maximum pressure average value taken.

It has been discovered that the drying rate of a liquid can be characterized quantitatively by measuring the increased pressure (or resulting apparent DST of a liquid). This measurement is based on the observation that the liquid may dry in the capillary tube and thus decrease the effective radius of the capillary tube, thereby increasing the pressure required to generate the bubbles. This increased pressure and related apparent DST are correlated to the drying rate of the liquid.

Thus, we have discovered that using the same principle as that used for the DST measurements, one can obtain the qualitative information about liquid drying rate. To do so one can design a new instrument capable of accurate measurements of the pressure at the capillary tip or use conventional DST tensiometers to monitor the pressure necessary to generate bubbles in a liquid through a capillary tube tip immersed in the liquid. At the beginning of the method, liquid enters the capillary (upward) and wets the inner capillary wall. The increasing gas pressure in the system gradually expels the liquid from the capillary and finally a bubble is formed at the capillary tip. When the liquid flows downward in the capillary, a thin liquid film is deposited on the inner capillary wall. The thickness of the film in the capillary depends on the liquid properties, e.g. viscosity. The gas flowing through the capillary is generally very dry as a necessary requirement due to the electronic system and pneumatic system elements that are sensitive for any condensation, e.g. water inside the instrument, such that the liquid film on the inner capillary wall will dry until it is re-wetted with another portion of the liquid that will re-enter capillary when the pressure in the capillary drops due to bubble release. During the DST measurements this cycle will be continuously repeated. For the liquids that are not perfectly non-drying or their dry films are not perfectly re-soluble, gradual clogging of the capillary can be visually observed and quantitatively observed through the increased pressure needed in order for the bubble to form in the smaller diameter capillary. The presence of deposit on the inner capillary wall will reduce the effective capillary radius and according to Equation (1) a higher pressure will be required to generate bubbles at the capillary tip. This phenomenon is schematically illustrated in the Examples 7-8 below. It has been discovered that the extent of the capillary clogging by the drying liquid depends on the drying/resolubility properties of the liquid. Therefore, this principle can be used to quantify the drying rate of the liquid, e.g. liquid printing inks.

Using the capillary clogging principle to characterize the drying/resolubility properties of the liquid one can measure the net effect. Generally, it was found that faster drying liquids had a greater slope of the curve of pressure needed in order to generate bubbles. Correspondingly, slower drying liquids had a smaller slope of the curve of pressure needed in order to generate bubbles.

Figure 2:
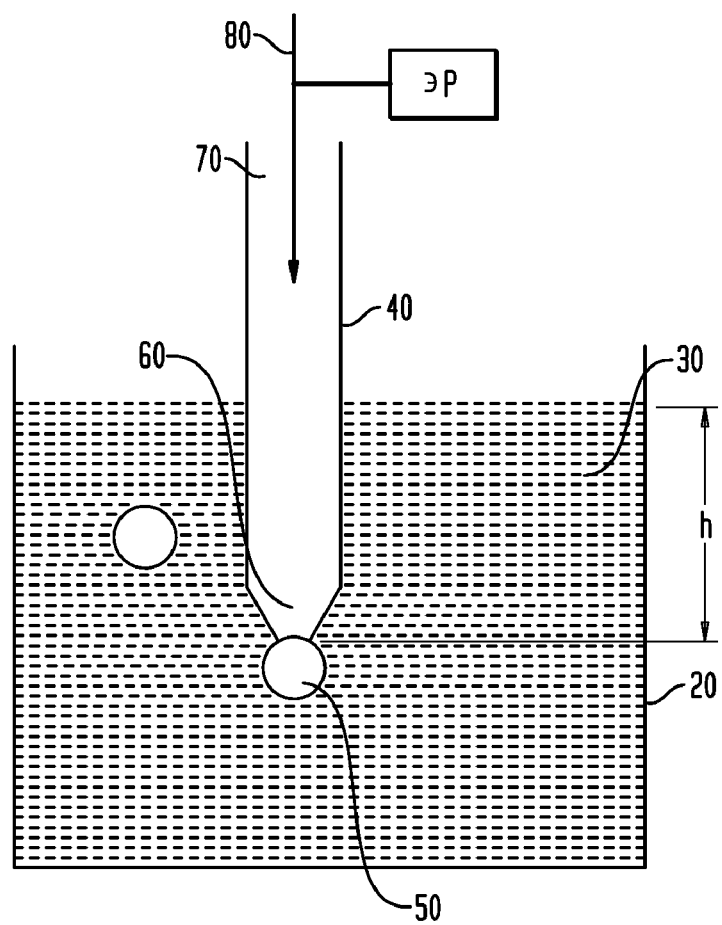
FIG. 2 is an overall view of an apparatus for measuring the drying rate of a liquid by measuring the pressure required to generate gas bubbles at a capillary tip immersed in the liquid.

According to FIG. 2, a single capillary apparatus for measuring the drying rate of a liquid as related to its apparent dynamic surface tension is described. A reservoir or container 20 for holding a volume of liquid 30, said volume not being critical and generally between about 20 to about 100 ml, although smaller or larger volumes may also be utilized, is provided. In order to meet the requirements of the apparatus, the volume of liquid 30 must be sufficient so that the formation of gas bubbles 50 in the liquid can readily be detected. The shape and materials of the liquid reservoir or container 20 is not critical. Typically, an open cylindrical glass or plastic beaker may be utilized. The material of the container 20 should be inert with respect to the liquid 30 whose drying rate is being determined. Glass, polyethylene, or polypropylene vessels are typically adequate for use with most liquids. If the liquid 30 has extreme pH values, typically either less than about 3 or greater than about 11, or is otherwise corrosive, a resistant material should be used for the material of the container 20. It is preferable that the material be translucent rather than opaque in order to facilitate observation of gas bubble formation in the volume of liquid 30 in the container 20.

To function as part of the apparatus, it is only essential that the capillary tube 40 be capable of being inserted into the liquid. The capillary tube 40, typically a cylindrical tube, of known inside diameter, is open at both ends. The capillary tube 40 has a first open end 60 for insertion into the volume of liquid 30 whose drying rate is being measured, present in the above-described container 20, and a second open end 70, to which a supply source 80 of an inert gas is capable of being attached. The capillary tube 40 may be made of any material that is inert to the liquid 30 whose drying rate is being measured. The material of the capillary tube 40 should be such that generally it is liquiphilic and it is not liquiphobic to the liquid 30 whose drying rate is being determined, so that the liquid 30 is capable of wetting the material of the capillary tube 40. The capillary tube 40 is typically glass, metal or plastic, and may be of any material that is not reactive with the liquid 30 or the inert gas 80. The length of the capillary tube 40 is not critical, and must only be sufficiently long to be able to draw a sample of the liquid 30 from the container 20 into the capillary tube 40 through its first open end 60 that is immersed into the volume of the liquid 30 in the container 20, and to be able to attach the supply source 80 of inert gas to the second, opposite open end 70 of the portion of the capillary tube 40 that remains above the liquid 30 in the container 20, in order to be able to direct a stream of inert gas into the capillary tube 40 downwardly and countercurrently to the upward direction in which the liquid 30 is drawn from the container 20 into the capillary tube 40. Typically, the capillary tube 40 has a length of from about 2 inches (about 5 cm) to about 4 inches (about 10 cm).

More than one capillary tube may be used and inserted into the liquid 30, e.g. Sensadyne PC9000 tensiometer that uses the DMBP principle has two capillaries of different orifices. If more than one capillary tube is used, then the pressure difference between the capillaries of different diameters is measured and taken into calculation of the DST.

The inert gas must not be chemically reactive with the liquid 30 whose drying rate is being measured. The inert gas should be capable of being delivered at a variable pressure. The pressure and the volume of the gas being delivered, should be capable of 40 being accurately measured. The inert gas utilized can be any gas that is inert to and not chemically reactive with the liquid whose drying rate is being measured. Typically, dry nitrogen is used, although other inert gases, including the noble gases, such as helium and argon may be used. The apparatus is used for determining the pressure (or the dynamic surface tension of the liquid 30) and accordingly the drying rate of the liquid 30 as set forth in the method below.

According to a method for determining the drying rate of a liquid utilizing the above-described apparatus, a volume of the liquid whose drying rate is to be determined is poured into a container. An inert gas supply source is then connected to the second open end of a clean capillary tube of known inside diameter and radius. The capillary tube is then positioned in the container of liquid such that the first open end of the capillary tube is immersed below the level of the liquid in the container in order for liquid to be drawn from the volume of liquid in the container into the capillary tube by the hydrostatic pressure and capillary action. It is preferred that the first open end of the capillary tubes be completely immersed below the liquid level in the container and the depth of immersion to be kept constant when comparing different samples.

The pressure of the inert gas should be noted. This pressure may increase upon time as the liquid may dry inside the capillary tube. During each cycle (generation of single bubble at the capillary tip) at first the liquid flows into the capillary (upward) due to capillary action and the hydrostatic pressure. After some time the liquid flow upward is stopped by the increasing gas pressure in the system. Further increasing gas pressure subsequently expels the liquid from the capillary (flow downward). At a certain time the pressure reaches the maximum value when the liquid meniscus curvature is equal to the radius of the capillary. Further pressure increase in the system causes instant bubble burst and release from the capillary. This causes the pressure in the system to drop and liquid re-enters the capillary upwards. Liquid exiting the capillary leaves the thin liquid film on the inner capillary wall. This film will dry (drying time) until it is re-wetted by the liquid re-entering the capillary and moving upward after bubble release (resolubilization time). The volatile matter from the liquid will be removed from the system by the stream of gas forming bubbles. If the semi-dry film is completely resolubilized during resolubilization time then no net deposit will be observed inside the capillary. All liquids other than perfectly non-drying or whose dry films are perfectly resoluble will gradually clog the capillary upon time. The rate of gas pressure increase in the system will depend on the extent of this clogging. Therefore monitoring this pressure can deliver information about drying properties of the liquid.

From the foregoing, it is evident that the apparatus and method of measurement for determining the drying rate of a liquid via the pressure measurements that is required to generate bubbles at a constant flow rate (or its apparent dynamic surface tension) are for use in the ambient atmosphere. It is to be understood that it is possible to measure the drying rate of a liquid under a different atmosphere by providing a different atmosphere in the capillary tube under which the liquid sample is drawn into the capillary tube. Thus, the temperature and/or humidity of the gas in the capillary tube can be controlled to provide such a different atmosphere. It is also possible to provide air, or a completely different atmosphere than air by providing a different gas in the capillary tube. Either of these can be accomplished in a number of ways, such as by placing the entire apparatus, including the capillary tube, in an enclosed hood into which air of a controlled temperature and humidity is introduced, or for a different, non-air atmosphere, by evacuating the air and introducing a different gaseous atmosphere of controlled and measured temperature and humidity.

Electric Method

Another apparatus and method to measure the drying rate of a liquid is disclosed by measuring the electrical resistance (ER) or electrical conductances (EC) of liquid films. EC of wet film is much higher than the EC of the dry film. Similarly, the electrical resistance of the wet film is much lower than the ER of dry film. Therefore, this technique can be applied to quantify the drying rate of any system that has different EC/ER in the wet and dry states without any limitations based on the liquid film's thickness, viscosity or drying speed.

It has been observed that the electrical conductance or resistance of active radiation curable (e.g. UV and EB curable inks, coatings and/or films) is slightly different on the top surface of said inks, coatings and/or films as compared to the bulk of the ink, coating and/or film. While not wishing to be bound by theory, it is assumed this difference is due to the inhibition of cure based on the presence of oxygen. The new method and apparatus operates below the surface where oxygen inhibition occurs and solves this problem and allows for more accurate measurements of the electrical resistance/conductance of both the bottom and the top layers of the ink, coating, and film as it dries.

Figure 3:
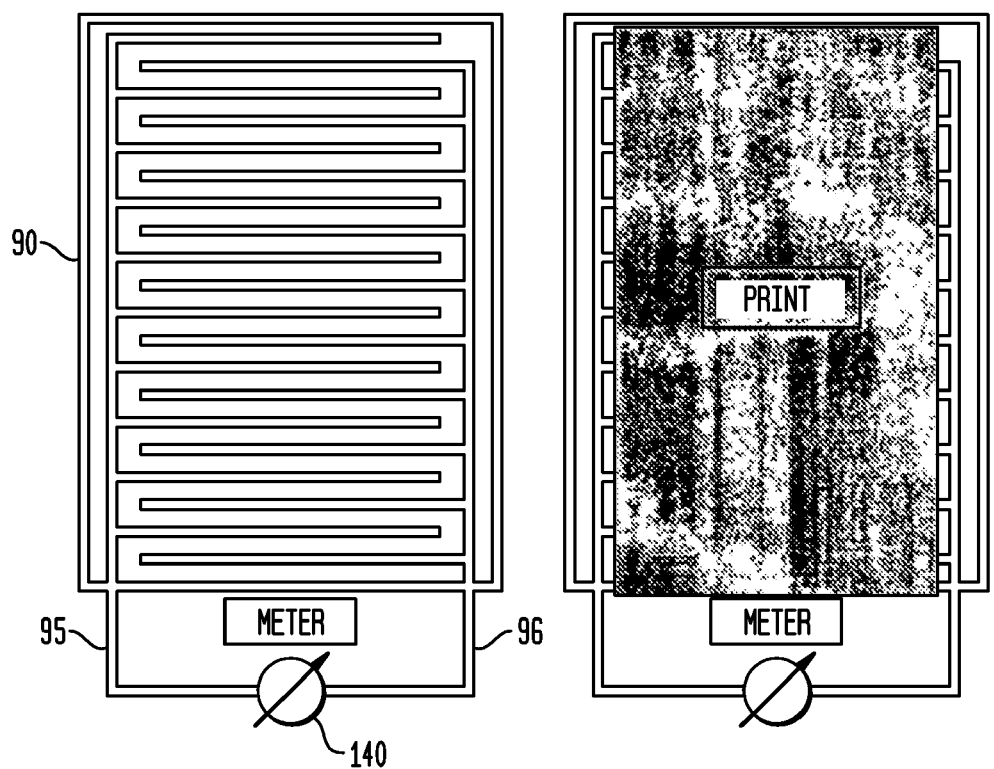
FIG. 3 is an overall view of an apparatus for measuring the drying rate of a liquid by measuring the electrical conductance or resistance of the liquid applied to a substrate.

A preferred embodiment of the invention is an apparatus to measure the electrical conductance or resistance of the surface of an energy curable ink, coating and/or film by contacting electrodes with the cured ink, coating and/or film (cured onto a substrate such as a Leneta® Board, plastic, glass or any other nonconductive substrate material that does not affect the electrical conductance of the liquid film being applied onto the substrate) and wherein the electrodes are connected to a measuring device. A pair of electrodes may be parallel or may have different forms such as a single pair of electrodes, a comb-type design or any other shape design. A comb-type electrode design is set forth in FIG. 3 wherein there are a pair of electrodes 95 and 96 have an inter-digitized configuration and are mounted on or in contact with a non-conductive material 90. The material which the inter-digitized electrodes are in contact with may be any non-conductive material, such as glass. In order to maintain contact between the electrodes and the cured ink, coating and/or film, a weight may be used to maintain pressure on the contact area between the cured liquid and the electrodes in contact with the non-conductive material.

In another embodiment of the invention, more than two electrodes may be placed in contact with the cured ink, coating and/or film. In either configuration the electrodes are connected to a measuring device. The length and gap between electrodes are such that the measurements can be performed in the resistance or conductance range accessible for easy and accurate measurements. The electrodes can be placed at different lengths apart from one another and may be different lengths themselves. Due to the micro-roughness of the cured film, physical contact between the cured film and electrodes is a key issue for this method such that the surface of electrodes achieves a good, reproducible result. Good contact can be achieved by using electrodes whose measuring surface is made of conductive soft rubber, elastomer, adhesive or high viscosity liquid. The last two options being highly suited for making off-line measurements.

The above apparatus is used to monitor electrical conductance or resistance of an energy curable ink, coating and/or film and can also be used to evaluate the degree of cure/drying rate of same. The measurement technique can be used off or on-line. For on-line applications the electrodes can take the form of a roller, the surface of which consists of conducting (e.g. conductive rubber) and insulating (e.g. non-conductive plastic) "rings". Said roller may be in contact with the coating surface and the electrodes may be connected to the recording device (e.g. resistance meter). It is recognized that the on-line configuration may be accomplished in a number of ways as known by those skilled in the art.

Figure 4:
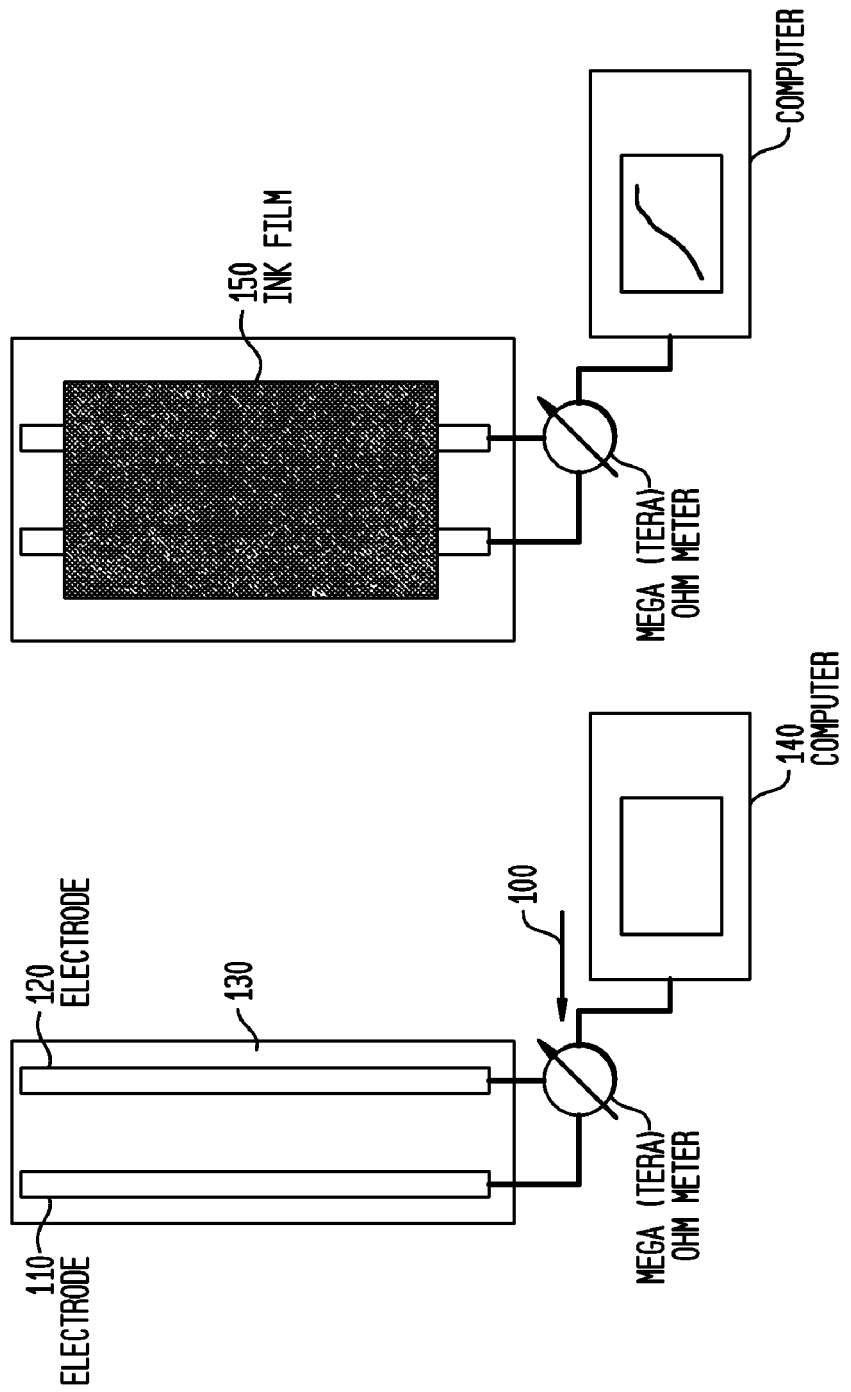
FIG. 4 is an overall view of an apparatus for measuring the drying rate of an energy cured liquid by measuring the electrical conductance or resistance with inter-digitized electrodes.

In another embodiment of the invention, apparatus 100 of FIG. 4, includes a pair of first 110 and second 120 strip electrodes that are disposed on a surface of a non-conductive substrate material 130 in a flat, co-planar manner, oriented in a generally parallel disposition with respect to one another. The set of electrodes 110, 120, can be made of different materials such as metal or conductive polymer, metal being preferred. The set of electrodes, 110, 120, can be placed in different lengths apart from one another and may be of different lengths themselves. The electrodes are attached to a means of measuring electrical conductance and/or resistance 140, such as an ohmmeter, resistivity meter or conductivity meter. The substrate 130 may be formed of Leneta® Board, plastic, glass or any other nonconductive substrate material that does not affect the electrical conductance of the liquid film being applied onto the substrate 130.

The method of determining the drying rate of a liquid film by measuring the liquid film's electrical conductance or resistance includes applying the liquid film onto the substrate (electrodes may be pre-printed thereon), by use of application apparatus which may be a handproofer or Meyer bar or any other way to apply the liquid film onto the substrate. Other forms of application of the liquid film may be employed. The electrodes measure the electrical conductance or resistance as the liquid film dries and the measurement is displayed on either an ohmmeter, resistivity meter, conductivity meter or similar measuring device. Where the measurement is of an energy curable ink, coating and/or film, the electrodes are simply placed in contact with the cured ink, coating and/or film. The method of the invention can be used for a wide variety of materials, including all types of printing inks, paints, coatings, varnishes, lacquers, adhesives and the like. The method is well suited for use in testing gravure and flexographic inks, including water based and solvent based inks and coatings for paper packaging, solvent based ink and coatings for film, and water based for film. The method can be used for any liquid system having different electrical conductance or resistance in the wet and dry states. There are no limitations on the method regarding the liquid's viscosity, ink film thickness; drying speed or chemistry.

According to the method for determining the drying rate of a liquid from either its electrical conductance, or inversely, its electrical resistance, it can also involve the preparation of a rollout sample of the liquid on a substrate. The liquid film is applied to a bare substrate, or a substrate having at least two electrodes preprinted thereon and attached to a resistivity (conductivity) meter. If the substrate is bare, then the electrodes are placed in contact with the top surface of the dried/cured liquid film (having been cured via an actinic radiation source such as ultraviolet light or electron beam) and the electrodes are also attached to a resistivity (conductivity) meter. The liquid film's electrical conductance or resistance is measured over a period of time. Liquid films have a relatively high electrical conductance that decreases as the liquid film dries. Thus, the drying rate may be calculated based on the decrease in the liquid film's electrical conductance. Correspondingly, the electrical resistance of wet liquid film is relatively low and increases as the liquid film dries. Again, the drying rate may be calculated based on the increase in the liquid film's electrical resistance. Graphs are to be plotted depicting the change in electrical resistance over time and the electrical conductance over time to obtain a characteristic determination and correlative drying rate.

From the foregoing, it is evident that the apparatus and method of measurement for determining the drying rate of a liquid film via the electrical conductance or resistance measurements are for use in an ambient atmosphere. It is to be understood that it is possible to measure the drying rate of a liquid under different experimental conditions such as increased atmospheric pressure, temperature, humidity, etc. Thus, for example, the temperature and/or humidity can be controlled in a measuring chamber. It is also possible to provide measurements in air or in a completely different atmospheric environment gas (e.g. nitrogen). Any of these conditions can be accomplished in a number of ways as known by those skilled in the art.

The following examples illustrate the invention. The examples use multiple colors (cyan and magenta and UV inks) of fast, medium and slow drying systems and said systems are applied on many substrates, including both a porous paper substrate and a non-porous substrate, using a conventional means.

Example 1

Flexomax® 33 (fast drying) and Flexomax® 039 (slow drying) cyan inks were measured separately to determine their respective drying rates. Each ink was applied to an Early Enterprises® 600 (2.8 BCM) handproofer with a volume of 2.8 BCM and rolled out onto a separate solid bleached sulfite paper liner ("SBS") and polypropylene film (AET Films®, T 523-3) via a disposable pipettes tip (Eppendorf pipet with 30 µl capacity). The rollout was made using constant angle, pressure and speed and the proof was heated for 10 seconds at 80° C. to dry the ink film. The first rollout was designated as Initial Rollout ("I"). After five minutes had passed, the ink was reapplied onto the handproofer, which contained some of the dried ink from the first application of the respective ink, and rolled out again for each ink on the substrate. The prints were heated as necessary in order to dry on the respective substrate. The second rollout was designated as After Rollout ("A"). The process was duplicated twice again on new substrates via new disposable Eppendorf pipet tips, in order to arrive at an average "I" and "A" for when the results were graphically plotted.

The inks left visual tails on each substrate. The tails of each ink in each of the three I and A rollouts were read with an X-Rite® 428 Densitometer, to obtain the print density of each tail. The average density of each tail for the three I and A rollouts was then plotted on a graph. The joining of each plotted density point on the graph formed a before (I) and after (A) drying proof curve, giving a fingerprint of the ink.

Figure 5:
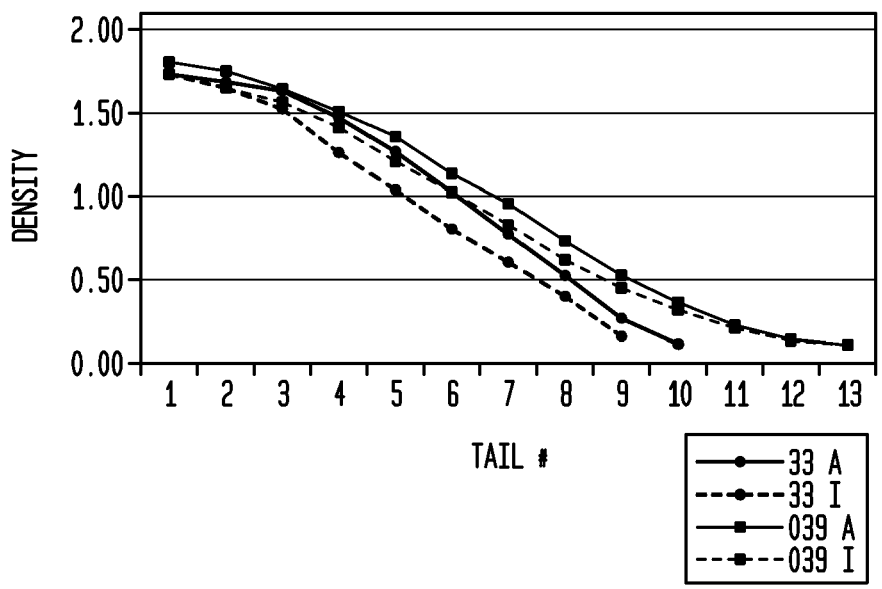
FIG. 5 illustrates graphs of the number of tails left by Flexomax® 33 and Flexomax® 039 inks drying on solid bleached sulfite paper (SBS) versus average initial (I) density and average after (A) density of the tails.
Figure 6:
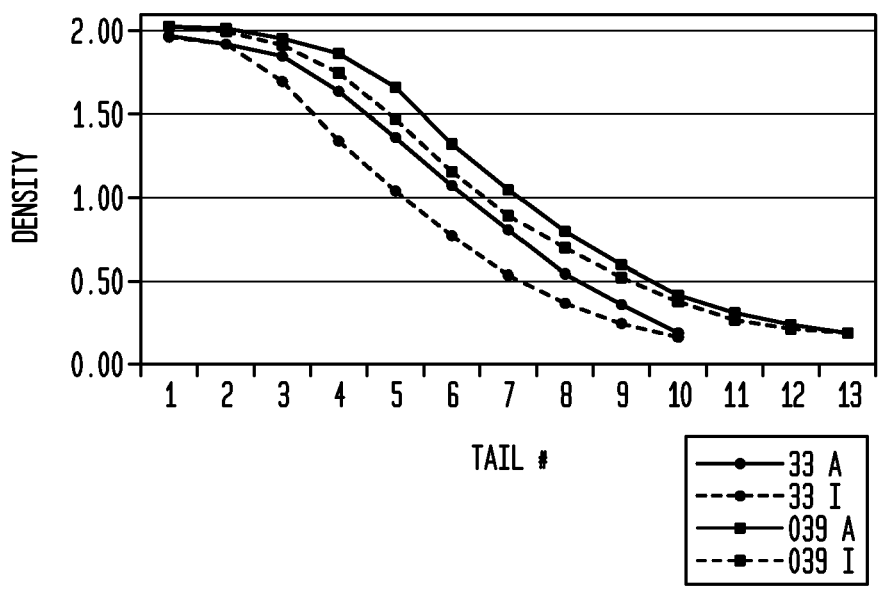
FIG. 6 illustrates graphs of the number of tails left by Flexomax® 33 and Flexomax® 039 inks drying on polypropylene film versus average initial (I) density and average after (A) density of the tails.

The inks were thus evaluated by comparing the respective drying profiles for each ink, which consist of a before drying proof curve and an after drying proof curve for each ink. Differences between the before and after drying proof curves are graphed to provide curve shapes. The parameters of the curves under comparison include differences in the slopes of the before and after drying proof curves for the two inks, the overall shapes of the before and after drying proof curves, and the area between the before and after drying proof curves. The graphs as plotted are in FIGS. 5 and 6.

The I curve represents the drying, transfer, and absorption of the ink. The A curve represents the drying, transfer, absorption, and resolubility of the ink. The number of tails represents the drying. The area between the A and I curves, the numbers of tails, the coefficients, and the curve shape and slope can be used to differentiate between the ink systems.

Observations drawn from the graphs are that the greater the number of tails, the slower the drying. Further, faster drying inks tended to have curves of greater slope than that for slower drying inks. Also, the curves for the faster drying inks tended to have a shorter tail and exhibit a greater area between the before and after drying proof curves. The overall area between the curves was greater for polymeric (e.g. polypropylene film) type substrates than for paper nitrocellulose based (e.g. solid bleached sulfite paper) type substrates, indicating less absorbency of the ink into the polymeric substrate. The area between the before and after drying curves for each ink was calculated and is shown in the following Table 1.

TABLE 1

| INK | SUBSTRATE | AREA |
|---|---|---|
| Flexomax ® 33 | SBS | 1.25 |
| Flexomax ® 039 | SBS | 0.82 |
| Flexomax ® 33 | Film | 1.68 |
| Flexomax ® 039 | Film | 0.91 |

The results of this test were verified as feasible on water-based systems by performing another test on UltraCorr GCMI® 74 Red Ink on SBS.

Example 2

Using the same equipment and same process as in Example 1, Sun Chemical® XV-98 33 magenta ink and 39 cyan ink were tested. And also Flexomax® 33 magenta ink and 039 cyan ink, were each tested on polypropylene film. The drying time between initial (I) and after (A) rollout was optimized so that the time between tests was five minutes for optimal results. For both systems (the Sun Chemical® XV-98 and Flexomax® inks) the magenta 33 ink had fewer tails, a greater slope and greater area between curves and therefore was observed as a faster drying ink. Using a Grind Gauge test for drying, it was determined that the Sun Chemical® XV-98 33 ink was the fastest drying ink and using a Geiger press to simulate ink resolubility, this same ink showed the least resolubility. The Sun Chemical® XV-98 33 ink demonstrated greater overall area between the curve, which was likely attributed to faster drying into the cells giving a greater slope, lower density and a greater amount of the ink drying into the cells. When the Sun Chemical® XV-98 33 ink was deposited for the A rollout, it resolubilized a greater amount of dried ink, giving a higher A curve. The area between the before and after drying curves for each ink was calculated and is shown in the following Table. This area corresponds to the resolubility and drying rate in the much faster drying 33 inks had a higher value than the 39 inks due to a greater amount of drying as shown in the cells of the I curve. The results are set forth in Table 2 below.

TABLE 2

| INK | | |
|---|---|---|
| Flexomax ® | Sun Chemical ® XV-98 | AREA |
| 33 | — | 1.61 |
| 039 | — | 0.72 |
| — | 33 | 1.08 |
| — | 039 | 0.67 |

Example 3

Figure 7:
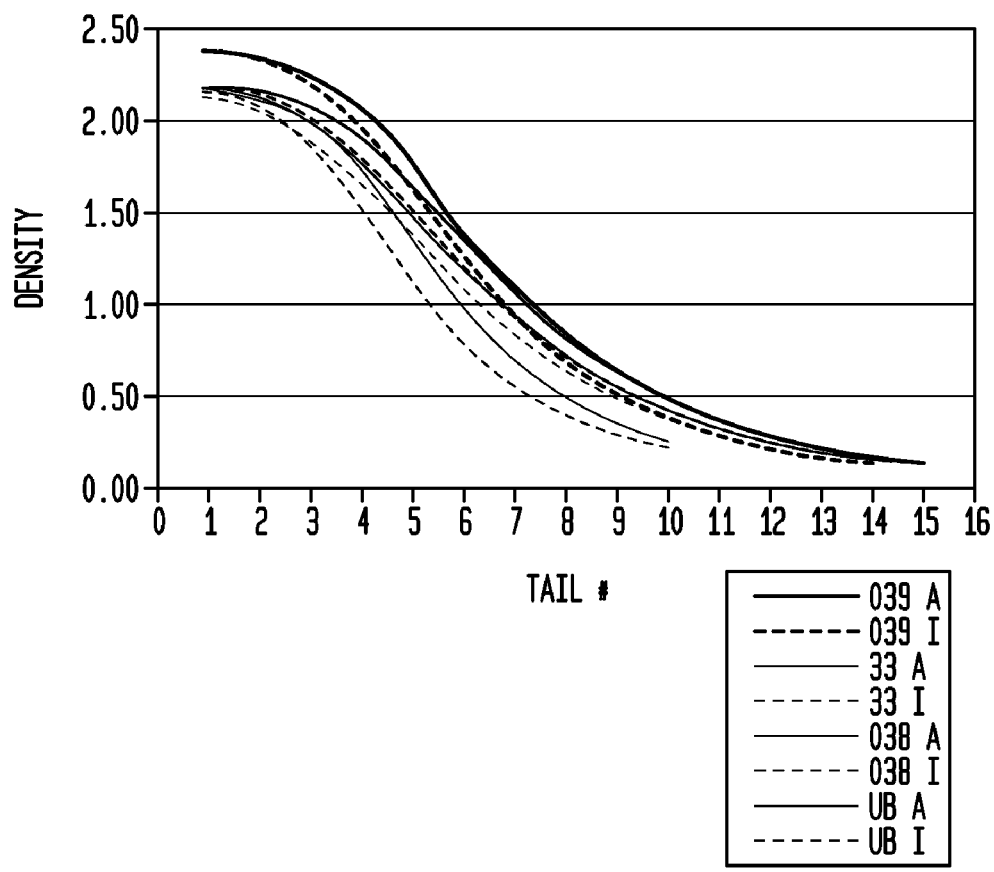
FIG. 7 depicts model I and A density curves fit to the raw density data of each tail versus tail number for Sun Chemical® XV-98 33, Flexomax® 039, Flexomax® 038, and Ultrabond® cyan inks tested on polypropylene film.

Using the same equipment and same process as in Example 1, Sun Chemical® XV-98 33, Flexomax® 039, Flexomax® 038, and Ultrabond® cyan inks were each tested on polypropylene film. A model curve was fit to the raw density data of each tail versus tail number and was graphed as set forth in FIG. 7.

Differences and trends were noted with respect to the base system. The model curves for the Sun Chemical® XV-98 33 ink had fewer tails, greater slopes and greater areas and thus was faster drying. The difference graph below shows four ink systems comprised of a colorant base and let down varnish—Sun Chemical® XV-98, Flexomax®, Sunfine® and Ultrabond®. The first three systems were shown with three base systems (33, 038, and 039). All systems demonstrated similar shapes with the bases. The fast drying 33 inks are not process printers in that the inks need not be slow drying for reproduction on a substrate. The magenta inks were then also tested and produced comparable results as with the cyan inks.

The results for area between the curves are shown in the following Table 3, wherein area corresponds to the drying rate and resolubility for the cyan inks:

TABLE 3

| INK | AREA |
|---|---|
| XV-98, 33 | 1.14 |
| XV-98, 038 | 0.95 |
| XV-098, 039 | 0.77 |
| Ultrabond | 1.07 |

Again, the 33 ink showed a greater area due to the much faster drying and higher ink deposit in the cells for the I curve.

Example 4

Using the same equipment and same process as in Example 1, water-based flexographic packaging inks were applied at a greater volume of 3.7 BCM and were tested for differences which would lead to tracking or poor trapping. Two cyan inks were tested, one with a low pH of 8.48 and the other with a high pH of 9.60. Differences were noted between cyan inks as a result of the pH of the cyan ink. The low pH cyan ink exhibited an area of 1.09 while the high pH cyan ink exhibited an area of 3.30. The high pH cyan ink therefore had a greater resolubility (area) and comparable drying rate versus the low pH cyan ink. These results were independently confirmed using other methods (i.e. grind gauge and electrical resistance) and the difference in volume from earlier tests did not affect the final results of the drying rate.

Example 5

Using the same equipment and same process as in Example 4, cyan inks containing different resins were evaluated to determine the effect of the resin on resolubility. Cyan ink was made by combination with three different resins (A—styrene acrylic 2, B—fumerated rosin ester, and H—styrene acrylic 1) and then each system was applied separately by the hand-proofer on T 523-3 substrate (polypropylene film). The three inks were tested in a trap with the white ink as the second down ink. The experiment was repeated with each cyan ink. The drying speeds of the three cyan inks were similar.

The resolubility of ink H by the white ink was much greater than that for ink B, which was greater than that for ink A. The high pH cyan ink of Example 4 was a remake of ink H.

For Examples 4 and 5, drying rate differences between inks of the same ink formula were attributable to the instability of the ink. The results for area between the curves, representing the drying and resolubility rate, are shown in the following Table 4:

TABLE 4

| INK | AREA |
|---|---|
| A | 0.77 |
| B | 1.96 |
| H | 3.54 |

As can be seen, the above method allows for quantification of the drying rate of liquid flexographic inks. The reproducibility of the results obtained by the method were independently confined in a separate experiment which yielded very good matching results.

Example 6

Figure 8:
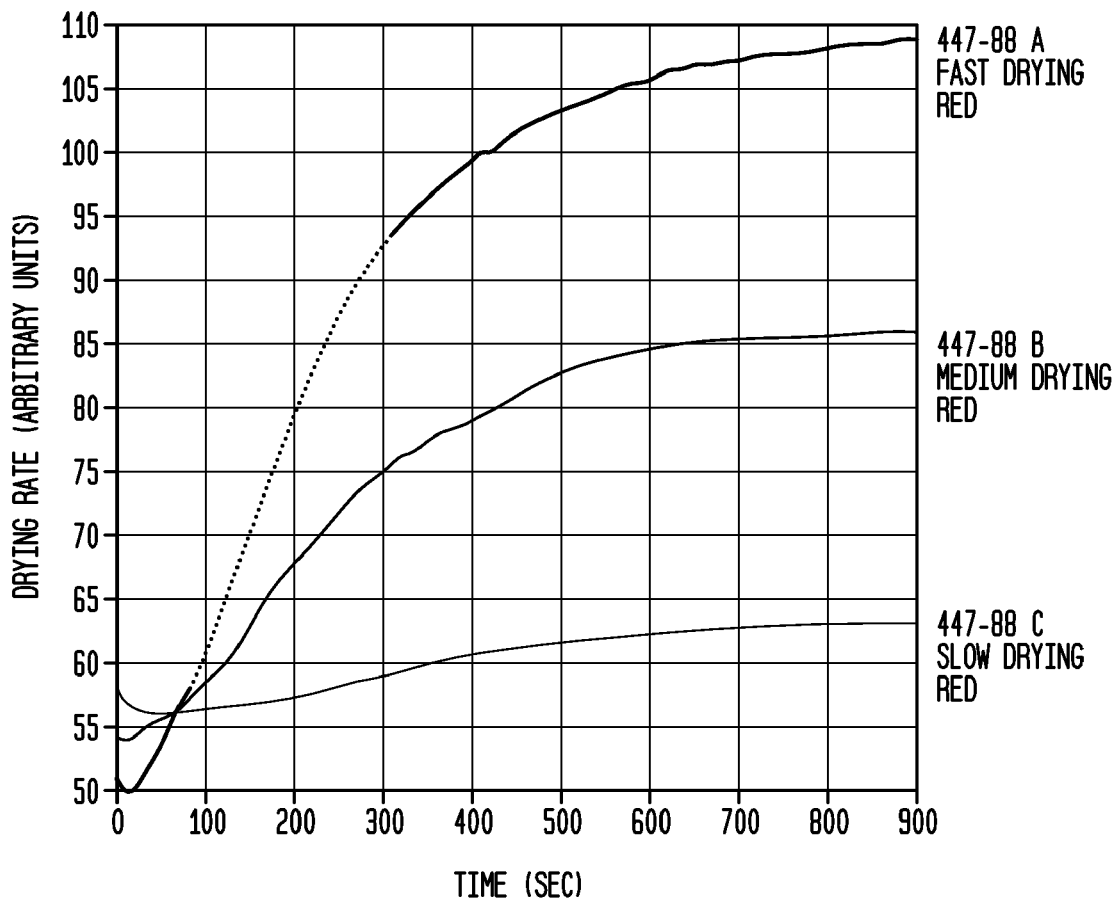
FIG. 8 shows the apparent DST values over a 15 minute time period obtained for three water based Flexographic Packaging Red inks (477-88 A, B and C) using a Sensadyne® PC500L instrument.

Examples 6, 7, and 8 refer to the apparatus presented in FIG. 2. For Example 6, three different samples of water based flexographic inks (Flexographic Packaging Red 477-88) carrying a manufacturer's'rating of either being "fast", "medium" or "slow" drying were placed in a container through which dry nitrogen was bubbled via a stainless steel capillary (0.5 mm in diameter). The pressure and the resulting apparent dynamic surface tension (DST) versus time of each ink was then noted using a Sensadyne® PC500L instrument (available from Sensadyne, Mesa, Ariz. and equipped with two stainless steel probes, one having a large orifice (4 mm in diameter) and the other having a small orifice (0.5 mm in diameter)). The instrument was calibrated using water and ethyl alcohol and the initial bubble rate was about 3 bubbles/second. The apparent DST for each ink was measured over 15 minutes respectively. The apparent DST value increased over time, due to ink drying inside the capillary, until it reached a plateau or steady state value. The difference between the initial and final apparent DST value represents the extent of ink drying and the slope of the curve represents the drying rate. The apparent DST values over the time period obtained for all three inks are presented in FIG. 8.

As can be seen, the graph clearly shows different "drying/resolubility profiles" for the inks drying at different rates.

Example 7

Figure 9:
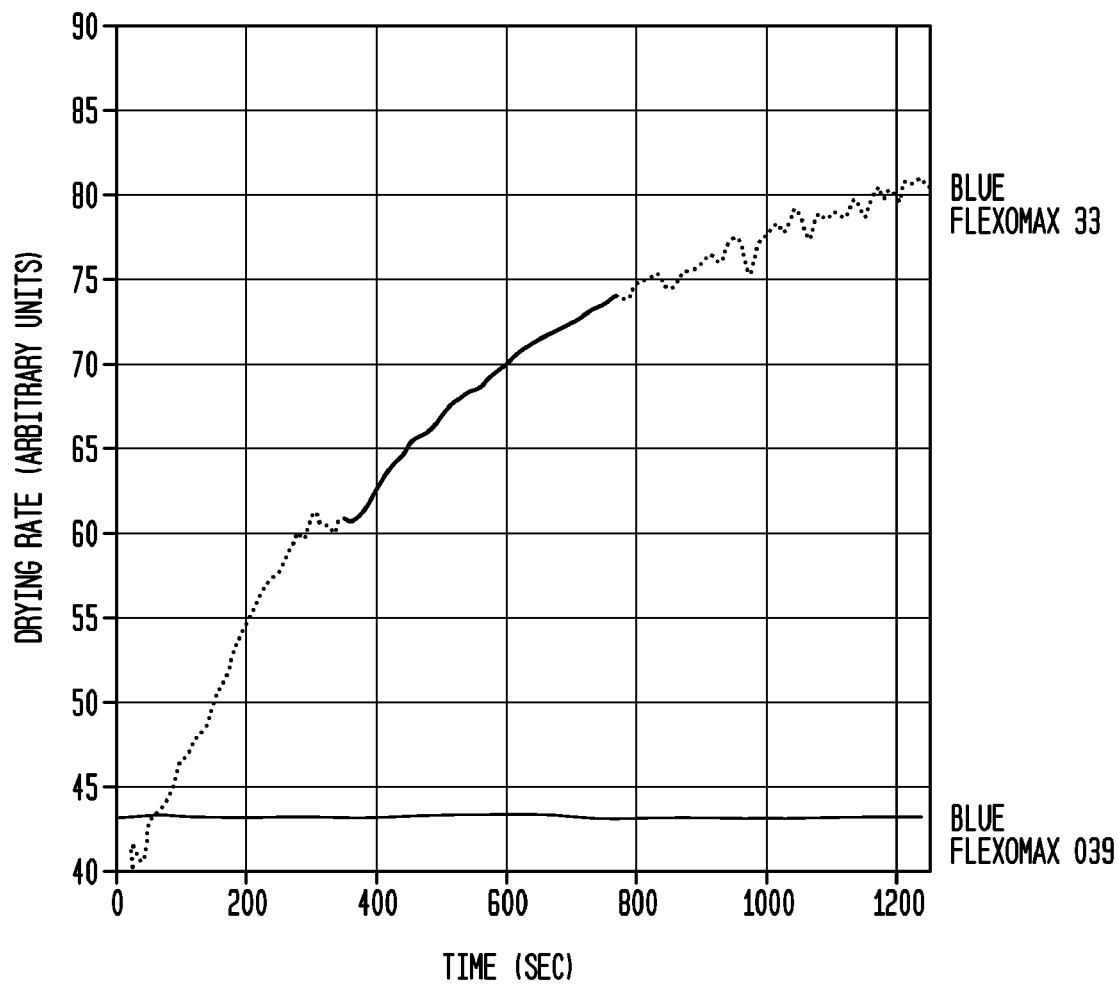
FIG. 9 shows the apparent DST values over a 20 minute time period obtained for solvent based laminating inks, Flexomax® 33 and Flexomax® 039, using a Sensadyne® PC500L instrument.

Using the same equipment and same process as in Example 6, solvent based laminating ink Flexomax® 33, carrying a manufacturer's rating of being a "fast" drying ink, and Flexomax® 039 carrying a manufacturer's rating of being a "slow" drying ink, were placed in the container and tested via their respective DST. The results obtained after measurements over a period of 20 minutes are shown in FIG. 9.

As can be seen, the above method allows for quantification of drying of liquid inks. The reproducibility of the results obtained by the method was independently confirmed in a separate experiment, which yielded very good matching results.

Example 8

Figure 10:
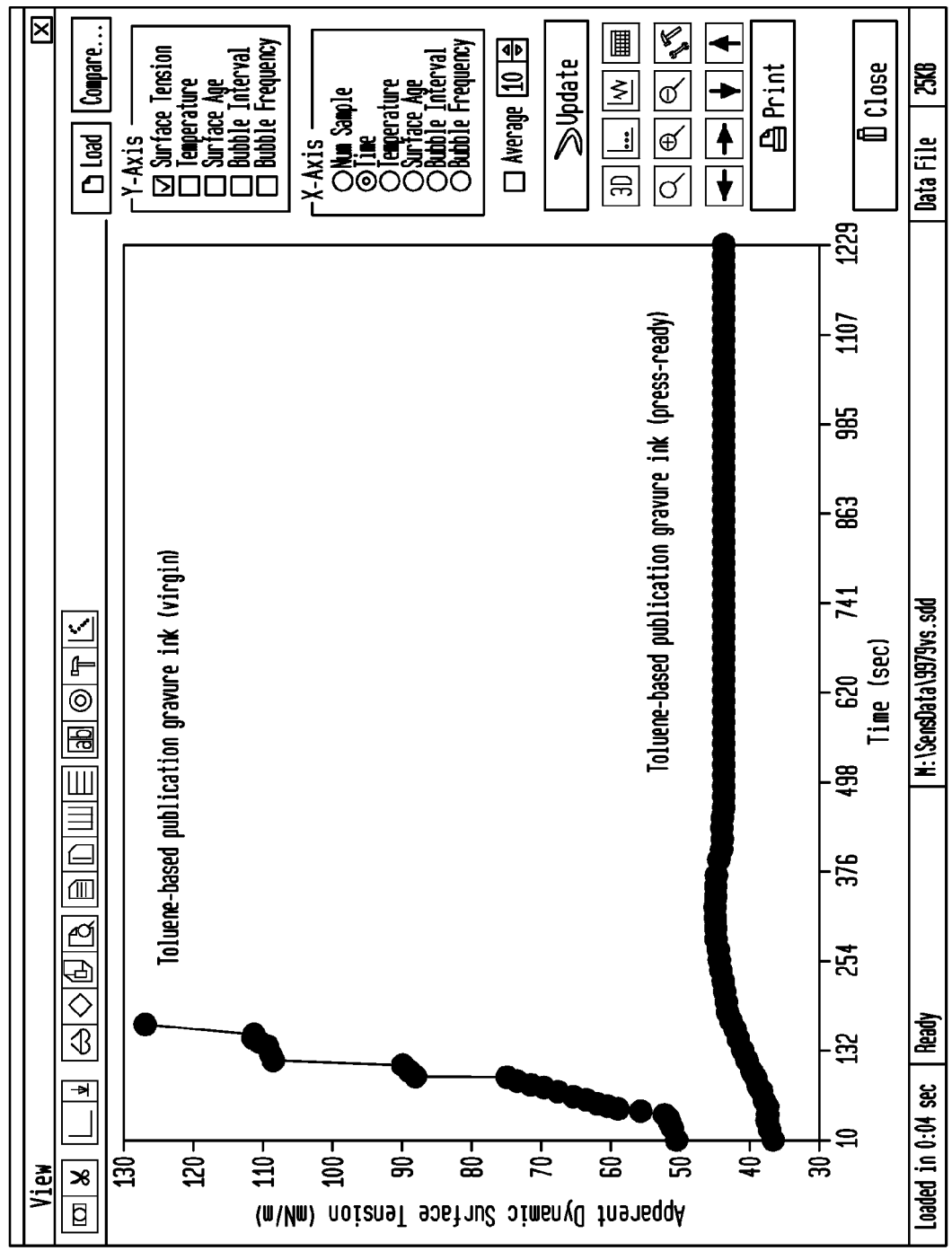
FIG. 10 shows the apparent DST values over a 20 minute time period obtained for two toluene based publication gravure inks using a Sensadyne® PC500L instrument.

Using the same equipment and same process, as described above in Example 6, two toluene based publication gravure inks (one containing high level of solids and the other diluted with toluene) were tested for their respective apparent DST to profile their drying rate. The results over a measurement of 20 minutes are shown in FIG. 10.

Example 9

Figure 11:
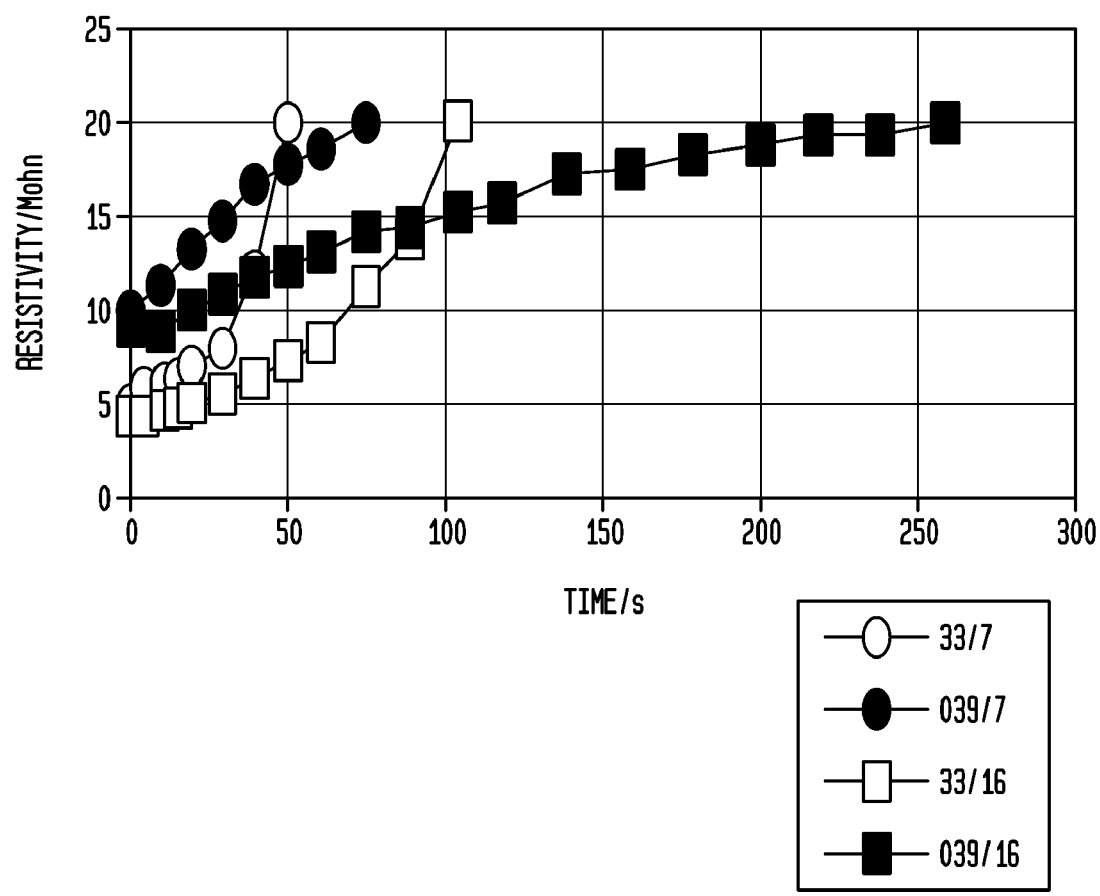
FIG. 11 shows the changes in ink film resistance recorded over a period of 5 minutes for solvent based laminating inks, Flexomax® 33 and Flexomax® 039, each of which were applied as thin film (33/7 and 039/7) and thick film (33/16 and 039/16) onto a Leneta® Board.

Examples 9 through 17 refer to the apparatus presented in FIG. 4. Solvent based laminating inks, Fleximax® 33 (fast drying) and Flexomax® 039 (slow drying), were applied via Meyer bars #7 (33/7 and 039/7—thin film) and #16 (33/16 and 039/16—thick film) onto a Leneta® Board having an imprinted electrodes on the surface of the Leneta® Board. The length of each pair of electrodes was 7 cm and the space between the electrodes was 0.3 cm. Changes in the inks film resistance was recorded using a Radioshack® multimeter (having a resistance range of 0-20 Mohm). The results obtained over a period of 5 minutes are presented in FIG. 11.

As can be seen, the ink film resistance depends on both the film thickness controlled by the respective Meyer bar used and the drying rate of the ink.

Example 10

Figure 12:
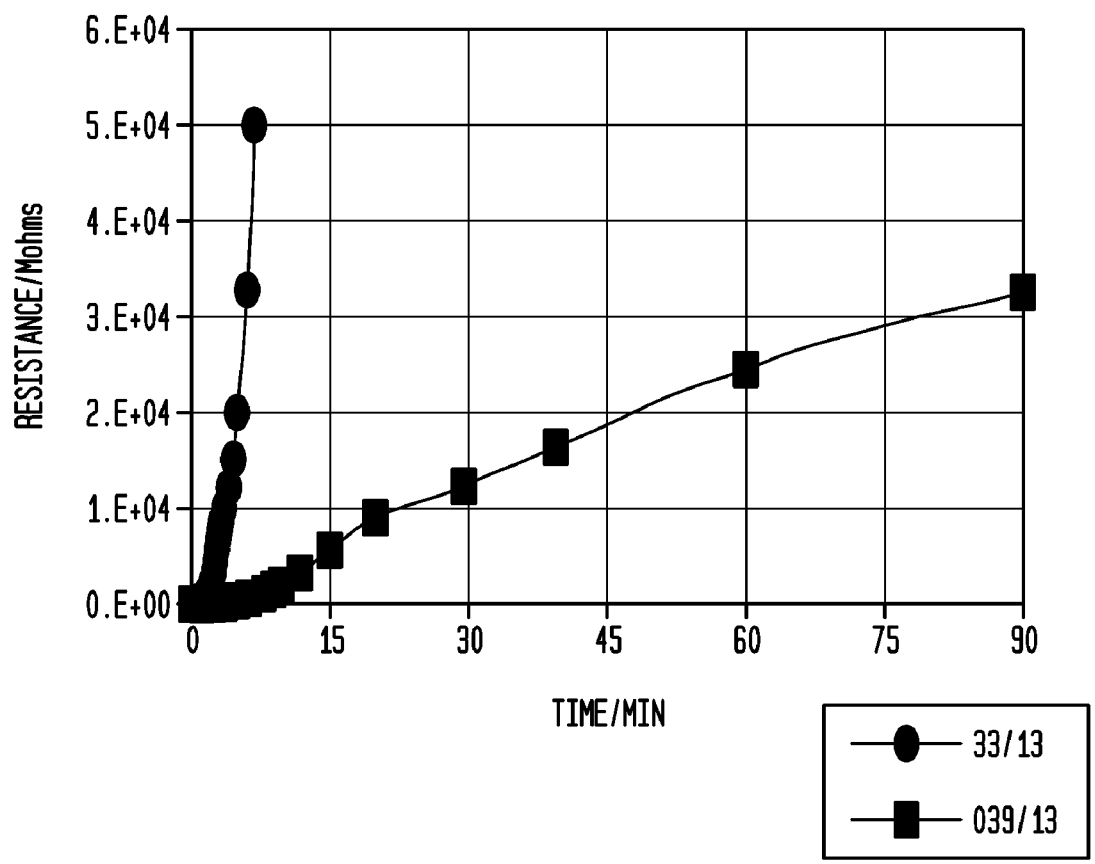
FIG. 12 shows the changes in ink film resistance recorded over a period of 90 minutes for solvent based laminating inks, Flexomax® 33 and Flexomax® 039, applied as 33/13 and 039/13 films onto a Leneta® Board.

Using the same inks as in Example 9, one bar was used, Meyer Bar #13 to, apply the inks stated above onto a Leneta® Board having a pair of electrodes imprinted which were 20 cm each and spaced 0.5 cm apart. The changes in ink film resistance were measured using a pair of electrodes imprinted which were 20 cm each and spaced 0.5 cm apart. The changes in ink film resistance were measured using a Fluke® 189 digital multimeter. The results obtained over a period of 90 minutes are presented in FIG. 12.

As can be seen, the resistance depends, on the drying rate of the ink. For a constant ink film thickness and under similar experimental conditions, film resistance over time for a given liquid will be a unique curve having a shape influenced primarily by the drying rate of the ink.

Example 11

Figure 13:
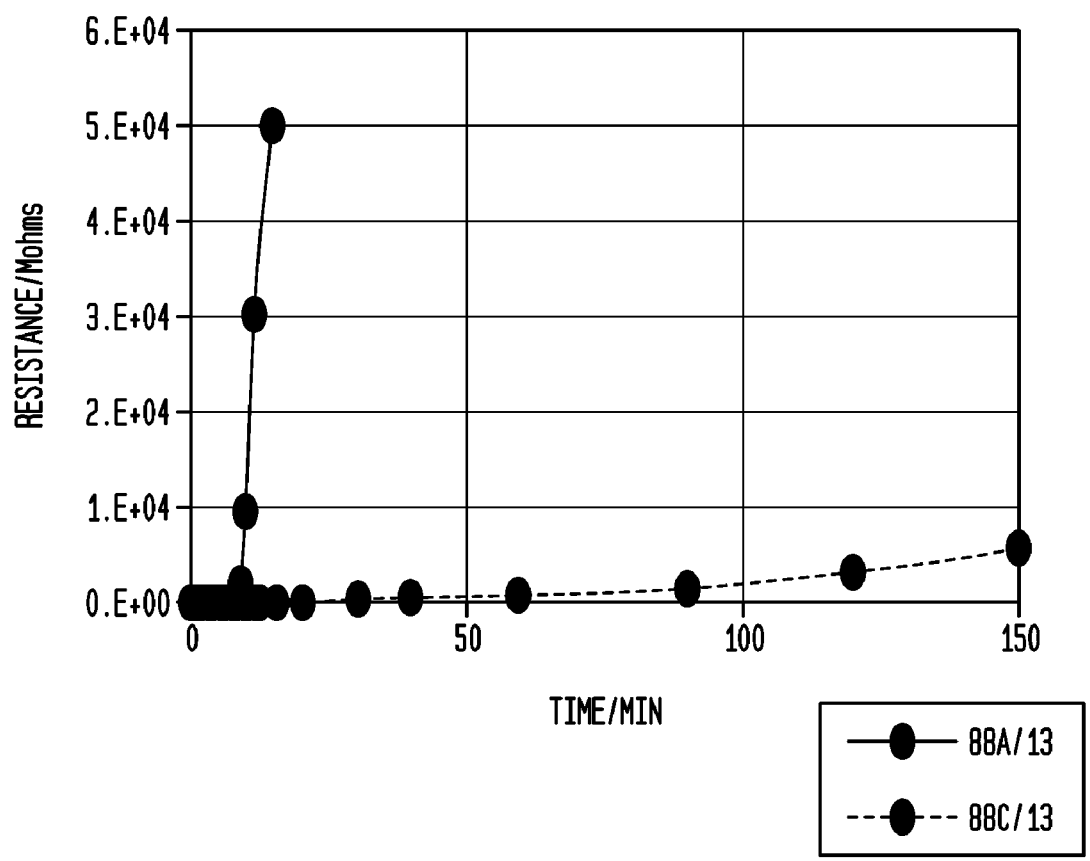
FIG. 13 shows the changes in the ink film's resistance measured over a period of 3 hours for water based flexographic inks, Sun Chemical® Flexographic Packaging Red 477-88 "fast" (A) and "slow" (C) drying, applied via Meyer Bar #13 onto a Leneta® Board.

Using the same equipment and same process as in Example 9, water based flexographic ink, Sun Chemical® Flexographic Packaging Red 477-88, carrying a manufacturer's rating of either being "fast" (A) or "slow" (C) drying, was applied on the substrate via Meyer Bar #13. The changes in the ink film's resistance were measured using a computer inter-faced, Fluke® 189 digital multimeter. The results obtained over a period of 3 hours are presented in FIG. 13.

As can be seen, the quantification method correlated well with the manufacturer's drying rate profile for each ink.

Example 12

Figure 14:
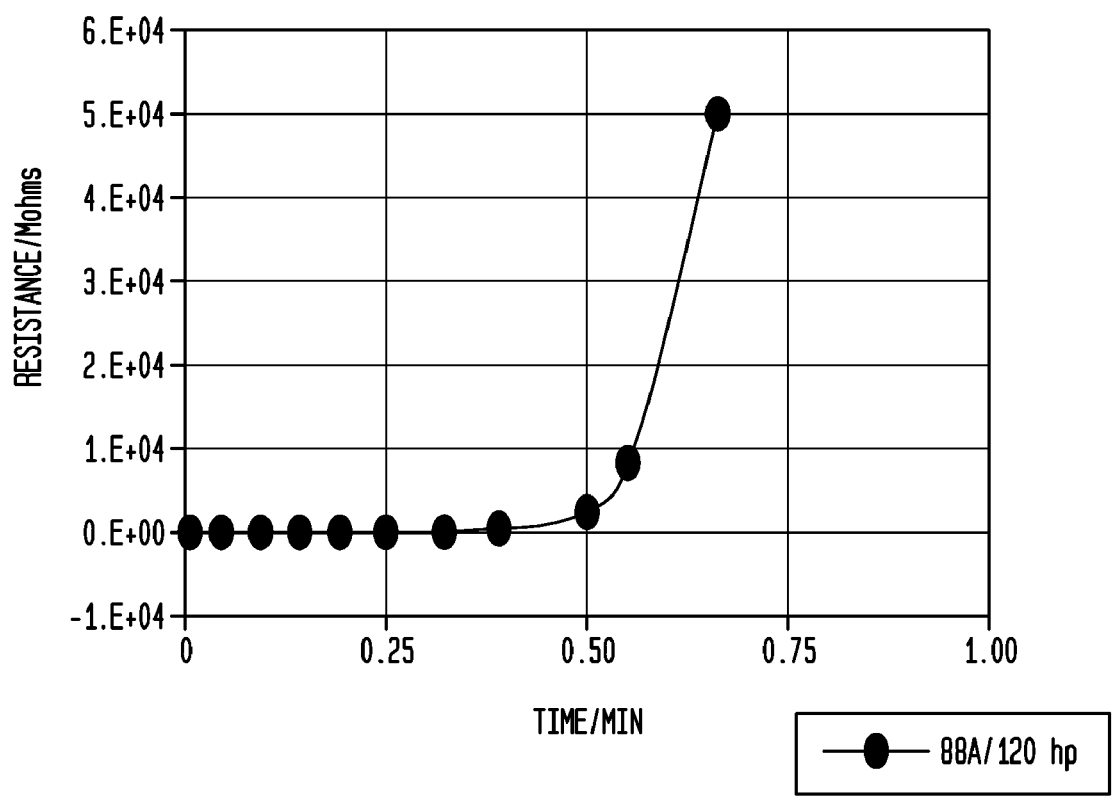
FIG. 14 shows the changes in the ink film's resistance measured over a period of 60 seconds for water based flexographic ink Flexographic Packaging Red 477-88 A applied to a Leneta® Board via a 120 lines per inch flexographic printing Early Enterprises® handproofer.

Using the same ink as in Example 11, the ink was applied to the Leneta® Board of Example 9, via a 120 lines per inch flexographic printing Early Enterprises® handproofer. The changes in the ink film's resistance were measured using a computer interfaced, Fluke® 189 digital multimeter. The results obtained over 60 seconds are presented in FIG. 14.

As can be seen, the quantification method applied to a very thin film correlated well with the drying rate profile of the ink.

Example 13

Using the same equipment and same process as in Example 12, an UV curable flexographic ink (FR Cyan FLHFV 5480055) and UV coating (R2964-156) were applied to the substrate. The changes in the ink film's resistance before and after curing were measured using a Fluke® 189 digitalmultimeter. The results are presented in Table 5 below.

TABLE 5

| Sample | UV Flexo Ink | UV coating |
| --- | --- | --- |
| Before curing | 59 Mohms | 359 Mohms |
| After Curing | 5,000 Mohms | 5,500 Mohms |

Example 14

Figure 15:
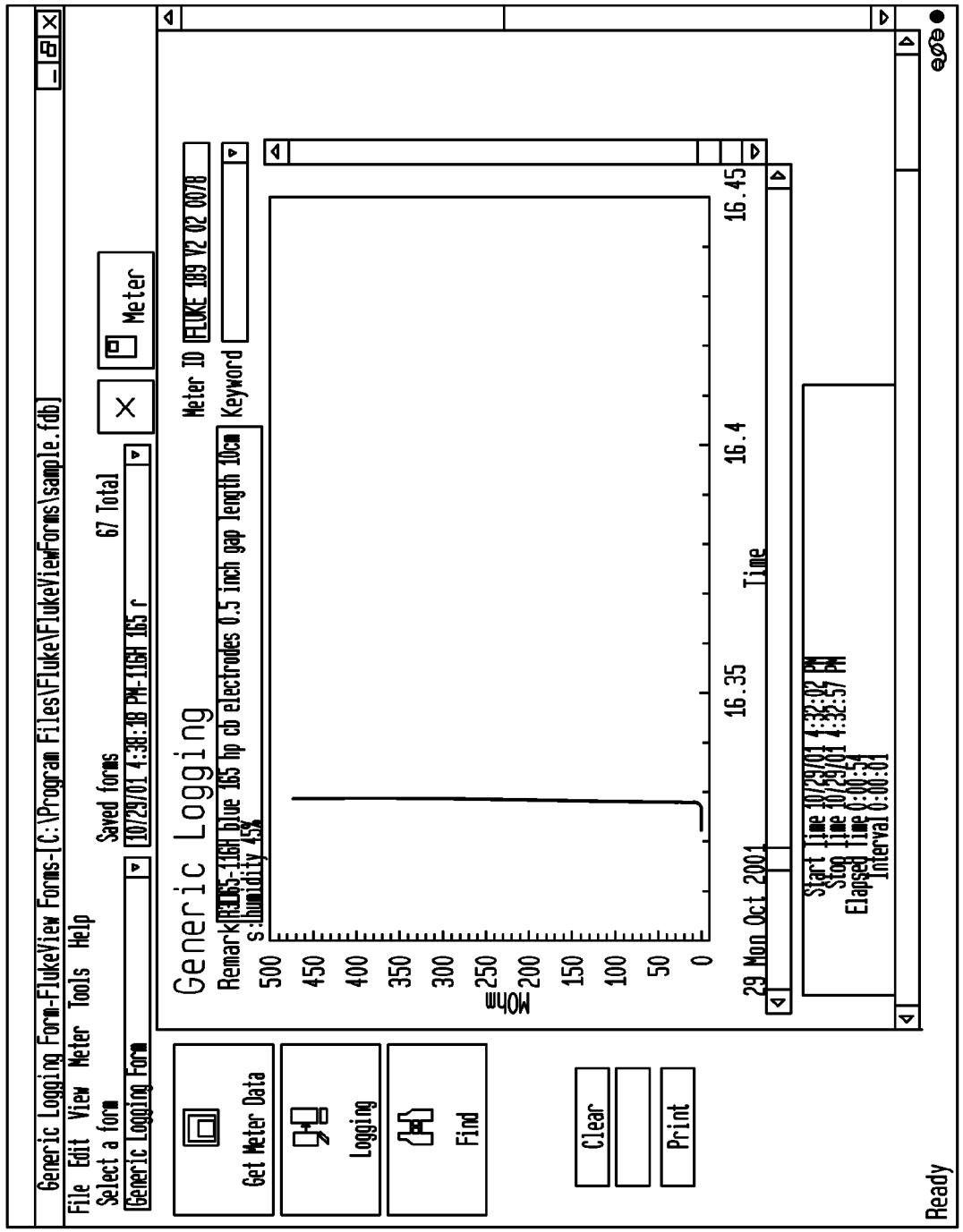
FIG. 15 shows the changes in ink film resistance measured at a humidity level of stabilized 45% humidity over a period of 15 minutes for a water-based blue laminating ink DPF-426 (Sun Chemical) via a flexographic handproofer (165 lines per inch) onto a Leneta® Board
Figure 16:
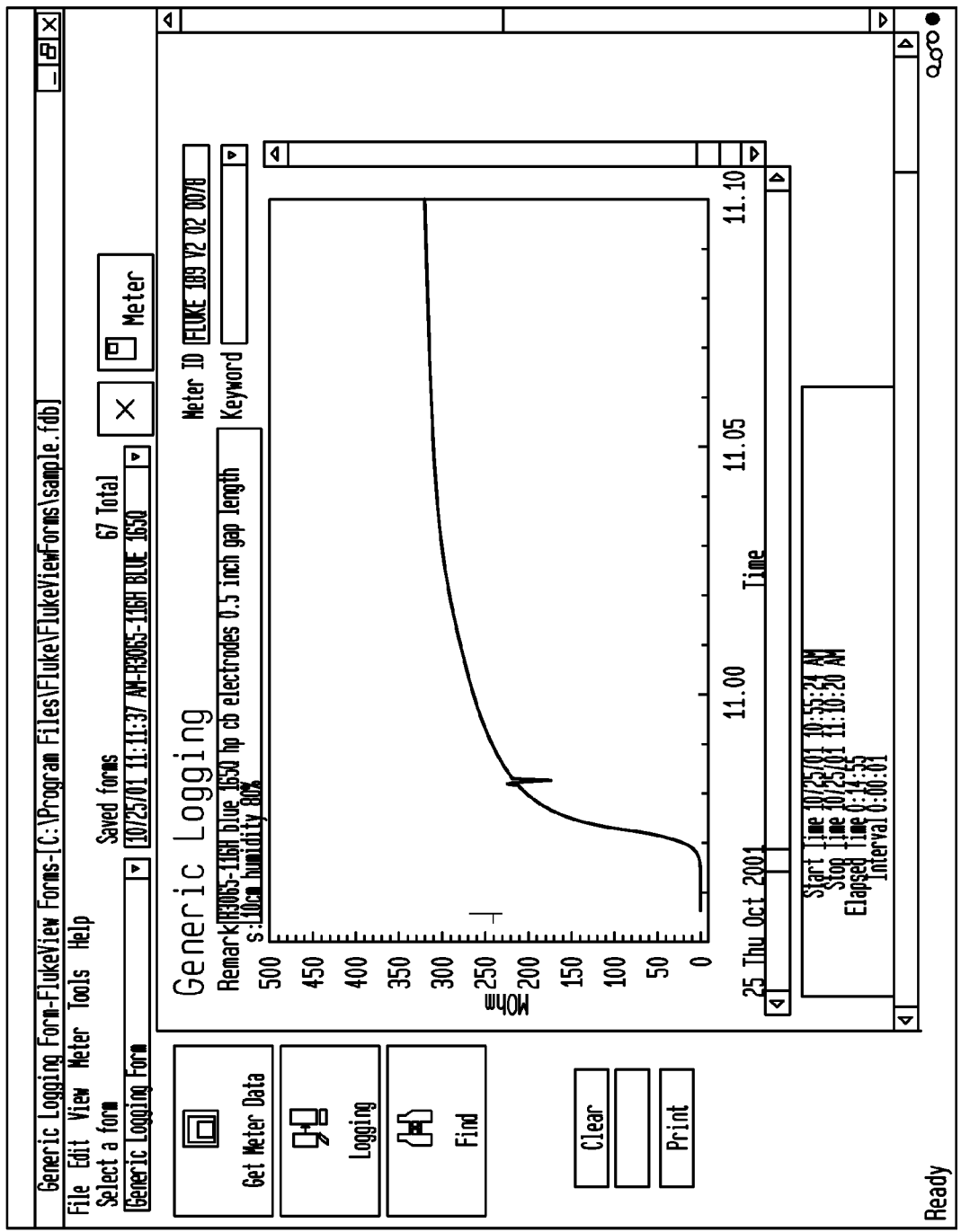
FIG. 16 shows the changes in ink film resistance measured at a humidity level of stabilized 80% humidity over a period of 15 minutes for a water-based blue laminating ink DPF-426 (Sun Chemical) via a flexographic handproofer (165 lines per inch) onto a Leneta® Board.

A water-based blue laminating ink (DPF-426, available from Sun Chemical) was applied via a flexographic hand-proofer (165 lines per inch) onto a Lenata® Board having 2 pairs of imprinted electrodes on the surface. The length of each pair of electrodes was 10 cm. and the space between the pair of electrodes was 1.25 cm. The measurements were performed at humidity levels of stabilized 45% and 80% humidity. Changes in ink film resistance were recorded with a Fluke® 189 digital multimeter (having resistance range of 0-500 Mohm). The results obtained over a measurement period of 15 minutes are presented in FIGS. 15 and 16.

As can be seen the results confirm that water based ink film dry faster at low humidity.

Example 15

Figure 17:
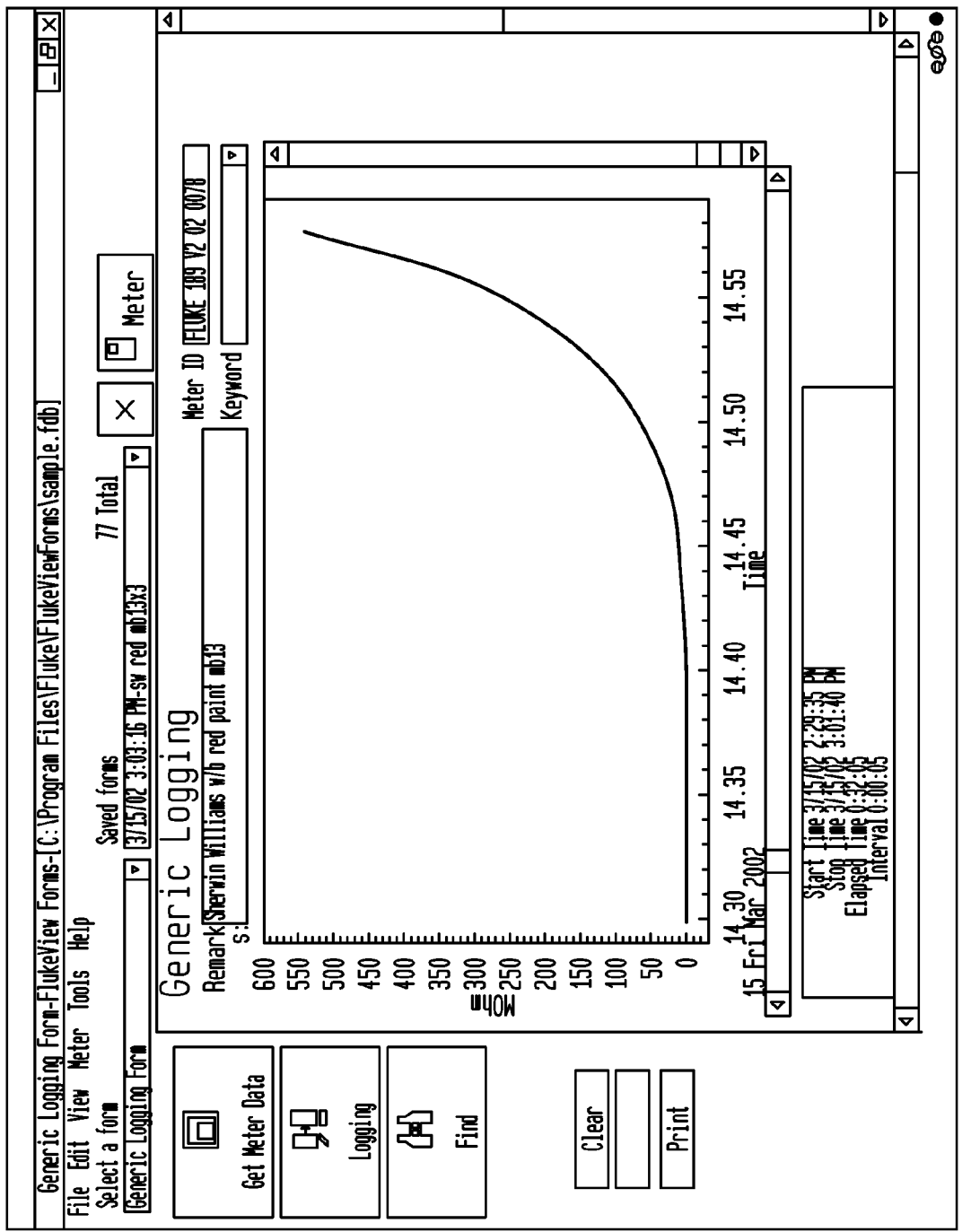
FIG. 17 shows the changes in ink film resistance recorded over a period of 30 minutes for a water-based paint (Sherwin Williams DTA Acrylic Gloss Coating, Safety Red B66 R38 136-559) applied via Meyer Bar #13 to a Leneta® Board.

A water-based paint (available from Sherwin Williams DTA Acrylic Gloss Coating, Safety Red B66 R38 136-559) was applied via a Meyer Bar #13 onto a Lenata® Board having a pair of electrodes the same length and spaced apart the same distance as described in Example 14 above. Change in the ink film resistance was recorded using the same Fluke® 189 digital multimeter as described in Example 14 above. The results obtained over a 30-minute period are presented in FIG. 17.

As can be seen, the results confirm that the method and apparatus can be used to profile the effect of additives on the drying rate of paints.

Example 16

Figure 18:
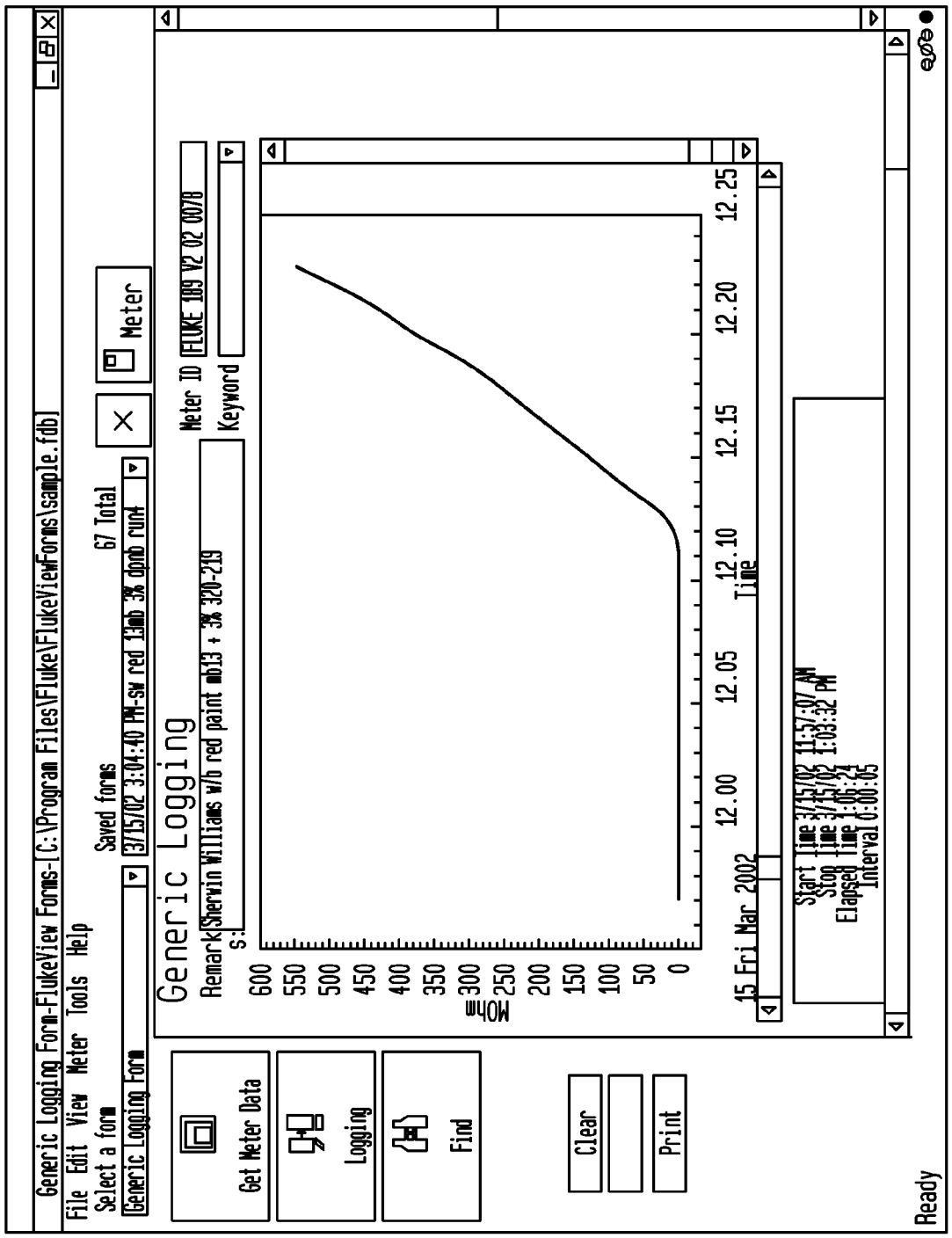
FIG. 18 shows the change in ink film resistance recorded over a period of 30 minutes for a water-based paint, (Sherwin Williams DTA Acrylic Gloss Coating, Safety Red B66 R38 136-559) to which dipropylene glycol (3%) was added, applied via Meyer Bar #13 to a Leneta® Board.

Diproplyene glycol (3%) was added to the water based paint of Example 15 and the modified paint was applied and tested via the same equipment and substrate as described in Example 15. Change in the ink film resistance was recorded over a 30-minute period and the results are presented in FIG. 18.

As can be seen, the results confirm that the method and apparatus can be used to profile the effect of additives on the drying rate of paints.

Example 17

The drying rate profiles of two solvent and one water-based automotive paint systems were measured using the procedure described in Example 16. The solvent based (n-butyl propionate) paint systems, one containing aluminum flakes and one containing a water based paint system containing aluminum flakes, were tested.

Figure 19:
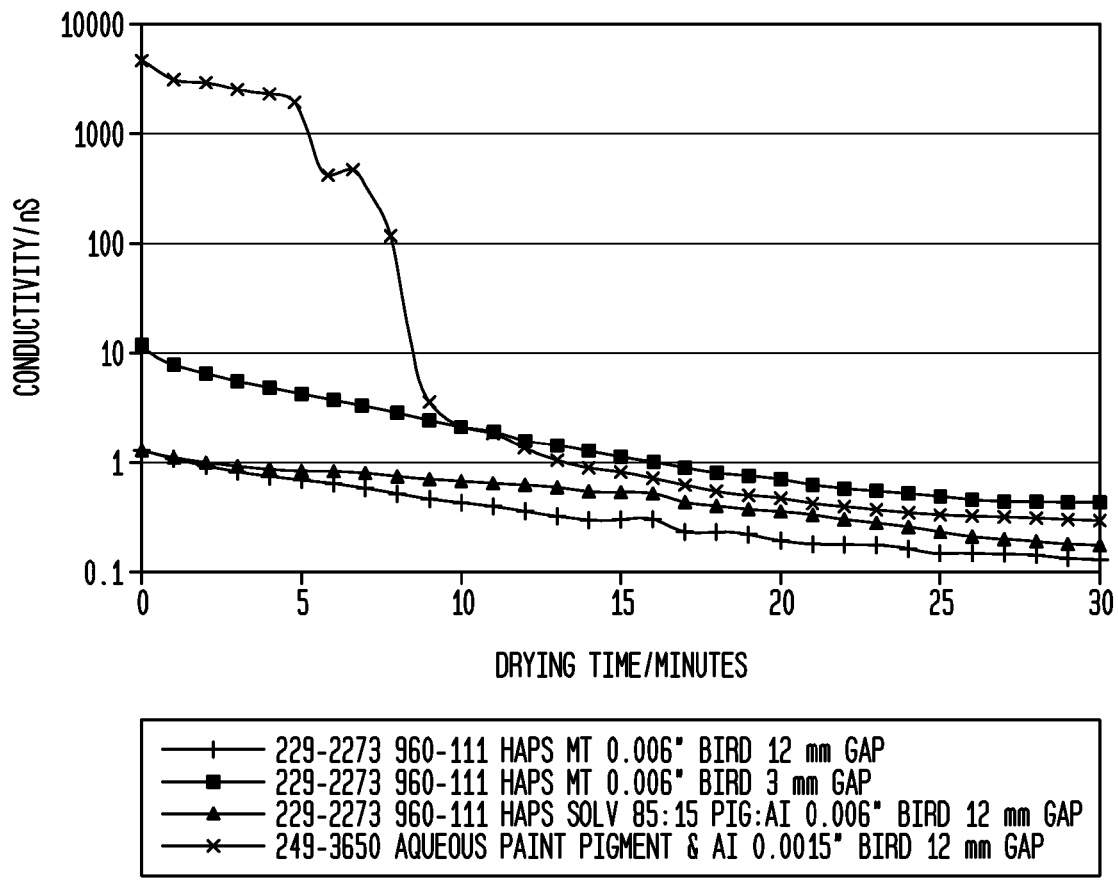
FIG. 19 shows the change in ink film resistance recorded over a period of 30 minutes for two solvent based paint systems, one solvent based paint system containing aluminum flakes and one water-based automotive paint system containing aluminum flakes, applied onto two different Leneta® Boards.

The three paints were each separately applied onto two different Leneta Boards, both having imprinted electrodes the same length as in Example 15 described above but with one pair of electrodes being spaced apart 1.25 cm. and the other pair of electrodes being spaced apart 3 mm. Change in the ink film resistance was recorded using the same Fluke 189® digital multimeter as in Example 15 described above. The results obtained over a 30-minute period are provided in FIG. 19.

As can be seen, the results confirm that the drying rate profile for water based automotive systems is dramatically different from that for solvent-based automotive paint systems. The method and apparatus were successfully used to profile drying rate of automotive paints.

Example 18

Figure 20:
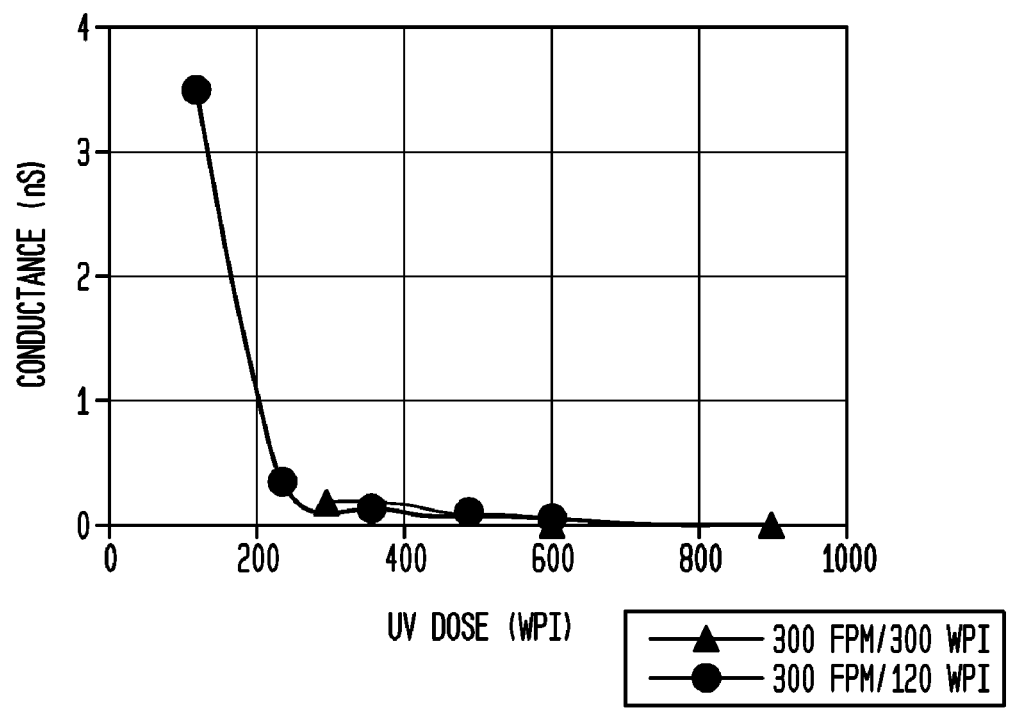
FIG. 20 shows the plot of electrical conductance versus UV dose for a UV coating applied onto a Leneta® Board using a Meyer Bar #3.

A UV coating was applied onto a Leneta® Board using a Meyer Bar #3. Using the apparatus of FIG. 3 (for Examples 18-21), a measuring pad with comb-type electrodes made of aluminum foil taped to Plexiglas (25×25 cm.) with the total length of the electrodes being ~900 cm (gap between the electrodes ~2 mm.) was used. The surface area tested was ~7×8 inches. The coating was cured gradually using a UV source (speed 300 fpm) and the resulting electrical surface conductance of the coating was measured using a comb-type electrode (10 lb. weight was used to keep constant pressure on the contact area between the sample and the electrodes). The plot of electrical conductance versus UV dose is presented in FIG. 20.

As can be seen substantial, there was a decrease in the coating surface conductance observed with increasing the dose of the UV radiation as correlating to cure/dry rate.

Example 19

Figure 21:
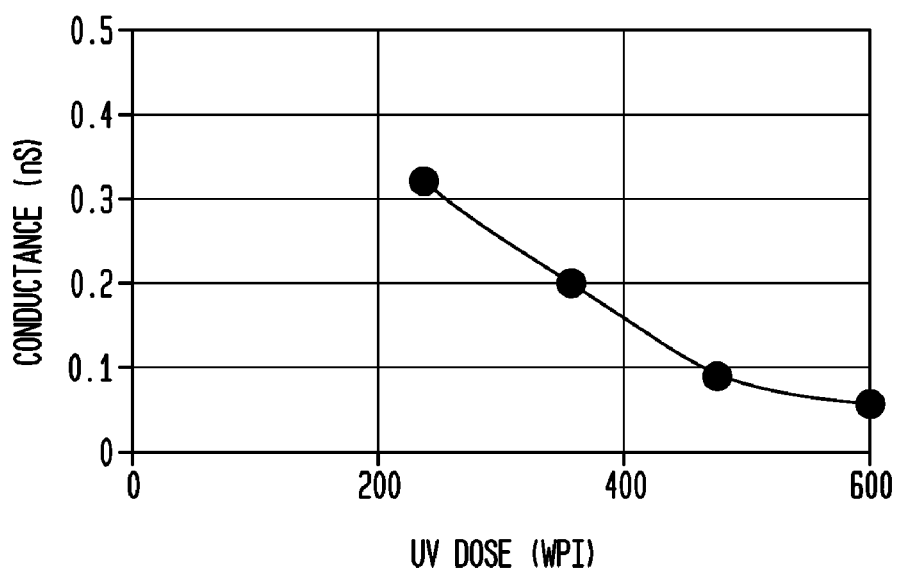
FIG. 21 shows a plot of electrical conductance versus UV dose for a UV coating applied onto a bi-axially oriented polypropylene (BOPP) film using a Meyer Bar #3.

A UV coating was applied onto a bi-axially oriented polypropylene (BOPP) film using a Meyer Bar #3. A measuring pad with comb-type electrodes made of aluminum foil taped to Plexiglas (25×25 cm.) with the total length of the electrodes being ~900 cm (gap between the electrodes ~2 mm.) was used. The surface area tested was ~7×8 inches. The coating was cured gradually using a UV source (speed 300 fpm) and the resulting electrical surface conductance of the coating was measured using a comb-type electrode (10 lb. weight was used to keep constant pressure on the contact area between the sample and the electrodes) and a Fluke 189 digital multi-meter (nanosiemens mode). The plot of electrical conductance versus UV dose is presented in FIG. 21.

As can be seen, there was a substantial decrease in the coating surface conductance observed with the increasing dose of the UV radiation as related to cure/drying rate.

Example 20

Figure 22:
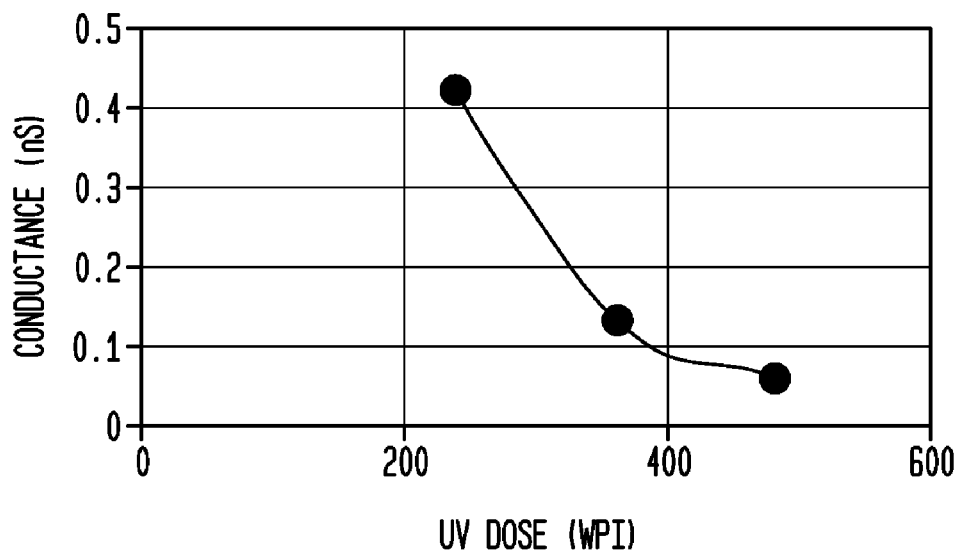
FIG. 22 shows a plot of electrical conductance versus UV dose for a UV coating applied onto a Leneta® Board using a Meyer Bar #3.

A UV coating was applied onto a Leneta® Board using a Meyer Bar #3. A measuring pad with comb-type electrodes made of aluminum foil taped to Plexiglas (25×25 cm.) with the total length of the electrodes being ~900 cm (gap between the electrodes ~2 mm.) was used. The surface area tested was ~7×8 inches. The coating was cured gradually using a UV source (speed 300 fpm) and the resulting electrical surface conductance of the coating was measured using a comb-type electrode (10 lb. weight was used to keep constant pressure on the contact area between the sample and the electrodes) and Fluke 189 digital multi-meter (nanosiemens mode). The plot of electrical conductance versus UV dose is presented in FIG. 22.

As can be seen, there was a substantial decrease in the coating surface conductance observed with the increasing dose of the UV radiation as related to cure/drying rate.

Example 21

Figure 23:
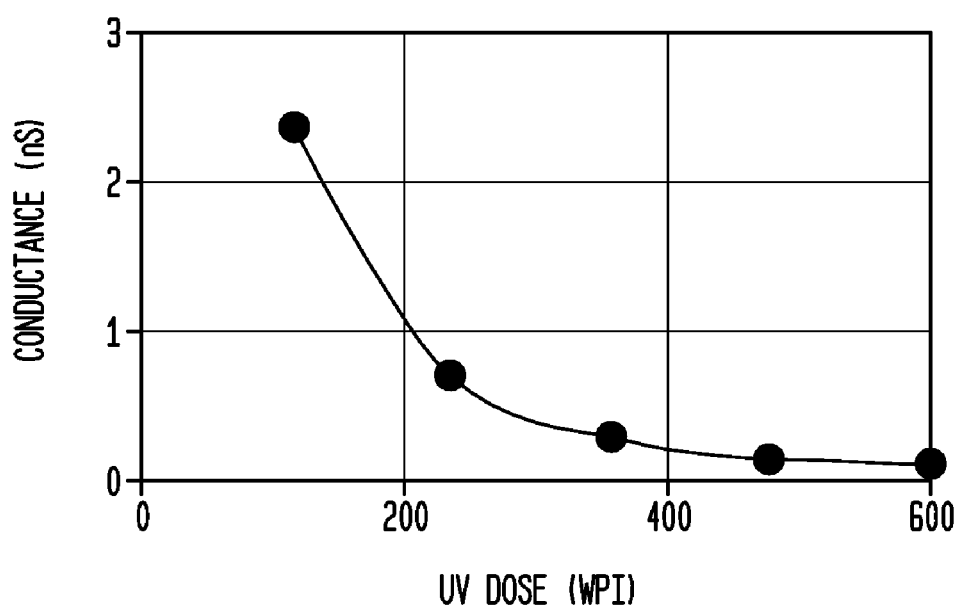
FIG. 23 shows plot of electrical conductance versus UV dose for a UV coating (containing 10% water) applied onto a Leneta® Board using a Meyer Bar #3.

A UV coating (containing 10% water) was applied onto a Leneta Board using a Meyer Bar #3. A measuring pad with comb-type electrodes made of aluminum foil taped to Plexiglas (25×25 cm.) with the total length of the electrodes being ~900 cm (gap between the electrodes 2 mm.) was used. The surface area tested was ~7×8 inches. The coating was cured gradually using a UV source (speed 300 fpm) and the resulting electrical surface conductance of the coating was measured using a comb-type electrode (10 lb. weight was used to keep constant pressure on the contact area between the sample and the electrodes) and a Fluke 189 digital multimeter (nanosiemens mode). The plot of electrical conductance versus UV dose is presented in FIG. 23.

As can be seen, there was a substantial decrease in the coating surface conductance observed with the increasing dose of the UV radiation as related to cure/drying rate.

The foregoing examples are not intended to be limiting. Other examples and applications will be apparent to persons of skill in the art. The scope of the invention is established by the following set of claims.

What is claimed is:

1. A method for determining the drying rate of a liquid film, comprising:
   (a) applying an amount of the liquid onto a first piece of a substrate to form an initial rollout proof having a head where the liquid is first applied to the substrate and at least one tail where the liquid is last applied to the substrate;
   (b) allowing the liquid to at least partially dry for a predetermined period of time;
   (c) repeating steps (a)-(b) to prepare at least one second rollout proof on a second piece of the substrate, said after rollout proof having a head where the liquid is first applied to the substrate and at least one tail where the liquid is last applied to the substrate, and allowing the second rollout to at least partially dry for the same predetermined period of time allowed to elapse in (b);
   (d) utilizing a densitometer to measure the density of each of the at least partially dried first and second rollout proofs, at the tails of the respective rollout proofs;
   (e) repeating steps (a)-(d) a plurality of times;
   (f) plotting the measured density of the tails of each of the respective rollout proofs versus a parameter related to the elapsed time at which the density measurement was made, to form a graph with at least one curve, which is representative of the drying rate of the liquid.

2. The method according to claim 1, wherein at least three replications of each sample are performed and average values of all of the measured density values for corresponding replications are plotted to form the graph.

3. The method according to claim 1, wherein in step (e), from 2 to 20 repetitions of steps (a)-(d) are performed until complete drying of the sample is attained, to provide a corresponding number of density measurements at the tails of the rollout proofs for use in plotting to form the graph of the curve representative of the drying rate of the liquid.

4. The method according to claim 1, wherein the liquid is selected from the group consisting of coatings, inks, and paints.

5. The method according to claim 1, wherein when the liquid is an ink.

6. The method according to claim 1, wherein when the liquid is a flexographic ink.

7. The method according to claim 6, wherein the flexographic ink is selected from the group consisting of: water-based ink for paper packaging, solvent-based ink for film, and water-based ink for film.

8. The method according to claim 1, wherein the at least one curve that is representative of the drying rate of the liquid is a plot of print density of the liquid, as measured by the densitometer at a predetermined point of time, versus sample number or tail number corresponding to that densitometer measurement.

9. The method according to claim 8, wherein the at least one curve representative of the drying rate of the liquid is selected from a plot of: average initial and average after density measurements versus sample or tail number; differences between the average after and average initial density measurements ($\Delta = \rho_A - \rho_I$) versus sample or tail number; and differences between the difference between the initial and after density and a density of a reference base substance ($\Delta = [(\rho_A - \rho_I) - \rho_R]$) versus sample or tail number.

10. The method according to claim 1, wherein step (f) is automated.

11. The method according to claim 10, wherein the automation of step (f) includes a computer system with computer graphics hardware and software, which is connected to the densitometer, such that densitometer measurements of the density of the tails of rollout proofs are directly inputted to the computer and the graph of the curve is automatically plotted.

* * * * *